United States Patent
Bristow et al.

(10) Patent No.: US 12,097,190 B2
(45) Date of Patent: *Sep. 24, 2024

(54) THERAPEUTIC USE OF LEVOROTATORY β-LACTAMS IN HEMATOPOIESIS, IMMUNO-ONCOLOGY THERAPY, AND REGULATION OF LIPOPROTEIN AND APOLIPOPROTEIN LEVELS

(71) Applicant: Alpha-1 Biologics, LLC, Stony Brook, NY (US)

(72) Inventors: Cynthia L. Bristow, Long Beach, NY (US); Ronald H. Winston, Santa Barbara, CA (US)

(73) Assignee: Alpha-1 Biologics, LLC, Stony Brook, NY (US)

( * ) Notice: Subject to any disclaimer, the term of this patent is extended or adjusted under 35 U.S.C. 154(b) by 234 days.

This patent is subject to a terminal disclaimer.

(21) Appl. No.: 17/739,648

(22) Filed: May 9, 2022

(65) Prior Publication Data

US 2022/0273626 A1    Sep. 1, 2022

Related U.S. Application Data

(60) Continuation of application No. 16/925,811, filed on Jul. 10, 2020, now Pat. No. 11,324,730, which is a
(Continued)

(51) Int. Cl.
*A61K 31/43* (2006.01)
*A61K 31/407* (2006.01)
(Continued)

(52) U.S. Cl.
CPC .......... *A61K 31/43* (2013.01); *A61K 31/407* (2013.01); *A61K 31/431* (2013.01);
(Continued)

(58) Field of Classification Search
CPC .. A61K 2300/00; A61K 31/407; A61K 31/43; A61K 31/431; A61K 31/545;
(Continued)

(56) References Cited

U.S. PATENT DOCUMENTS

| | | |
|---|---|---|
| 5,760,027 A | 6/1998 | Buynak et al. |
| 6,858,400 B2 | 2/2005 | Bristow |

(Continued)

FOREIGN PATENT DOCUMENTS

| | | |
|---|---|---|
| CA | 982557 | 1/1976 |
| CN | 101003539 | 7/2007 |

(Continued)

OTHER PUBLICATIONS

Ahajournals.org [Online], Gordon et al., "Abstract 29: Alpha-1-antitrypsin Protects High Density Lipoprotein From Functional Inactivation by Elastase," Arteriosclerosis, Thrombosis, and Vascular Biology, Jan. 2017, [Retrieved on Apr. 20, 2023], retrieved from URL<https://www.ahajournals.org/doi/10.1161/atvb.36.suppl_1.29>, 5 pages.

(Continued)

*Primary Examiner* — Savitha M Rao
(74) *Attorney, Agent, or Firm* — Fish & Richardson P.C.

(57) ABSTRACT

A method for increasing the number of CD4+ T-lymphocytes in the serum of a subject in need of such treatment comprising administering to the subject a pharmaceutical
(Continued)

composition comprising an amount of an L-isomer of β-lactam effective to increase the number of CD4+ T-lymphocytes in said patient's serum.

4 Claims, 13 Drawing Sheets

Related U.S. Application Data division of application No. 16/544,774, filed on Aug. 19, 2019, now Pat. No. 10,709,693, which is a division of application No. 15/874,694, filed on Jan. 18, 2018, now Pat. No. 10,413,530.

(60) Provisional application No. 62/447,689, filed on Jan. 18, 2017.

(51) Int. Cl.
| | | |
|---|---|---|
| *A61K 31/431* | (2006.01) | |
| *A61K 31/545* | (2006.01) | |
| *A61K 31/546* | (2006.01) | |
| *A61K 39/395* | (2006.01) | |
| *A61K 45/06* | (2006.01) | |
| *A61P 11/00* | (2006.01) | |
| *A61P 35/00* | (2006.01) | |

(52) U.S. Cl.
CPC .......... *A61K 31/545* (2013.01); *A61K 31/546* (2013.01); *A61K 39/39533* (2013.01); *A61K 45/06* (2013.01); *A61P 11/00* (2018.01); *A61P 35/00* (2018.01)

(58) Field of Classification Search
CPC ............ A61K 31/546; A61K 39/39533; A61K 45/06; A61P 11/00; A61P 35/00
See application file for complete search history.

(56) References Cited

U.S. PATENT DOCUMENTS

| | | |
|---|---|---|
| 6,887,678 B2 | 5/2005 | Bristow |
| 10,413,530 B2 | 9/2019 | Bristow et al. |
| 10,709,693 B2 | 7/2020 | Bristow et al. |
| 11,324,730 B2 | 5/2022 | Bristow et al. |
| 2010/0137194 A1 | 6/2010 | Lawrence et al. |
| 2012/0172286 A1 | 7/2012 | Bristow |
| 2014/0005108 A1 | 1/2014 | Bristow |
| 2018/0221349 A1 | 8/2018 | Bristow et al. |
| 2020/0016128 A1 | 1/2020 | Bristow et al. |
| 2020/0383955 A1 | 12/2020 | Bristow et al. |

FOREIGN PATENT DOCUMENTS

| | | |
|---|---|---|
| DE | 2208582 | 9/1972 |
| WO | WO 2013/042122 | 3/2013 |

OTHER PUBLICATIONS

Vasudevan et al., "Preferred conformations and flexibility of aminoacyl side chain of penicillins," International Journal of Biological Macromolecules, 1982, 4(6):347-351.

Bangalore et al., "Comparison of properties of membrane bound versus soluble forms of human leukocytic elastase and cathepsin G," Biol. Chem. Hoppe. Seyler., Oct. 1994, 375(10):659-666.

Bashir et al., "α-1 antitrypsin gene exon use in stimulated lymphocytes," J. Clin. Pathol., Sep. 1992, 45(9):776-780.

Bristow et al., "Inhibition of HIV-1 by modification of a host membrane protease," Int. Immunol., Feb. 1995, 7(2):239-249.

ClinicalTrials.gov [online], "Safety and Efficacy of (α1Proteinase Inhibitor, α1PI) in HIV Disease," NCT01731691, Apr. 2012, last updated Aug. 31, 2020, retrieved from URL<https://www.clinicaltrials.gov/study/NCT01731691>, 12 pages.

Cvetovich et al., "An Asymmetric Synthesis of L-694,458, a Human Leukocyte Elastase Inhibitor, via Novel Enzyme Resolution of β-Lactam Esters," J. Org. Chem., 1996, 61(19):6575-6580.

Dion et al., "Estimating thymic function through quantification of T-cell receptor excision circles," Methods Mol. Biol., 2007, 380:197-213.

(56) References Cited

OTHER PUBLICATIONS

Donskoy et al., "Gated importation of prothymocytes by adult mouse thymus is coordinated with their periodic mobilization from bone marrow," J. Immunol., Oct. 2003, 171(7):3568-3575.
International Preliminary Report on Patentability in International Appln. No. PCT/US2018/014258, mailed on Aug. 1, 2019, 16 pages.
Krutzik et al., "Fluorescent cell barcoding in flow cytometry allows high-throughput drug screening and signaling profiling," Nat. Methods, May 2006, 3(5):361-368.
Lorcheim, "Chlorine Dioxide Gas Inactivation of Beta-Lactams," Applied Biosafety, 2011, 16(1):34-43.
Mulchande et al., "Synthesis, stability, biochemical and pharmacokinetic properties of a new potent and selective 4-oxo-β-lactam inhibitor of human leukocyte elastase," J. Enzyme Inhib. Med. Chem., Apr. 2011, 26(2):169-175.
Shulman et al., "Lymphocyte crawling and transendothelial migration require chemokine triggering of high-affinity LFA-1 integrin," Immunity, Mar. 2009, 30(3):384-396.
Wilmouth et al., "Mechanistic Insights into the Inhibition of Serine Proteases by Monocyclic Lactams," Biochemistry, Jun. 1999, 38(25):7989-7998.
Winkler et al., "Serine protease inhibitors serpina1 and serpina3 are down-regulated in bone marrow during hematopoietic progenitor mobilization," J. Exp. Med., Apr. 2005, 201(7):1077-1088.
Ali et al., "Thrombin Primes Responsiveness of Selective Chemoattractant Receptors at a Site Distal to G Protein Activation (*)," Journal of Biological Chemistry, 1996, 271(6):3200-3206.
Avis et al., Remington: The science and practice of pharmacy, vol. 2, 1995, parenterals pp. 1624-1651).
Berge et al., "Pharmaceutical Salts," J.Pharm. Sci, 1977, 3 pages.
Bonney et al., "Pharmacological profile of the substituted Beta-lactam L-659286: A member of a new class of human PMN elastase inhibitors," J Cell Biochem, 1989, 39: 47-53.
Bristow et al., "[alpha]1Proteinase Inhibitor Regulates CD4+ Lymphocyte Levels and Is Rate Limiting in HIV-1 Disease," PLOS One, Feb. 2012, 7: e31383.
Bristow et al., "A Feedback Regulatory Pathway Between LDL and Alpha-1 Proteinase Inhibitor in Chronic Inflammation and Infection," Discov. Med., 2013, 16:201-218.
Bristow et al., "HIV-1 preferentially binds receptors co-patched with cell surface elastase," Blood, 2003, 102:4479-4486.
Bristow et al., "NF-kB Signaling, Elastase Localization, and Phagocytosis Differ in HIV-1 Permissive and Nonpermissive U937 Clones," J. Immunol, 2008, 180:492-499.
Bristow et al., "Self antigen prognostic for human immunodeficiency virus disease progression," Clin. Diagn. Lab. Immunol., 2001, 8:937-942.
Bristow et al., "Specific activity of α1 proteinase inhibitor and α2 macroglobulin in human serum: Application to insulin-dependent diabetes mellitus," Clin. Immunol. Immunopathol, 1998, 89:247-259.
Bristow et al., "T cell antigen receptor immune complexes demonstrating biologic and proteolytic activity," International Immunology, 1993, 5(1):79-88.
Bristow et al., "α1Antitrypsin therapy increases CD4+ lymphocytes to normal values in HIV-1 patients in Soluble Factors Mediating Innate Immune Responses to HIV Infection," (ed. M.Alfano) (Bentham Science Publishers, http://www.benthamdirect.org/pages/openAccess.php, 2010).
Bristow, "Slow human immunodeficiency virus (HIV) infectivity correlated with low HIV coreceptor levels," Clin. Diagn. Lab. Immunol., 2001, 8:932-936.
Cao et al., "Endocytic receptor LRP together with tPA and PAI-I coordinates Mac-I-dependent macrophage migration," EMBO J, 2006, 25:1860-1870.
CLSI. MIOO-S24: Performance Standards for Antimicrobial Susceptibility Testing; Twenty-Fourth Informational Supplement, 2014, 230 pages.

Dementiev et al., "Active Site Distortion is Sufficient for Proteinase Inhibition by Serpins: Structure of the covalent complex of alproteinase inhibitor with porcine pancreatic elastase," Journal of Biological Chemistry, 2006, 281:3452-3457.
EP Search Report in European Appln. No. 0167293.8, dated Nov. 20, 2020, 7 pages.
Fagerberg et al., "Analysis of the Human Tissue-specific Expression by Genome-wide Integration of Transcriptomic and Antibody-based Proteomics," Mol. Cell. Proteomics, 2014, 13:397-406.
Ferraz et al., "Development of novel ionic liquids based on ampicillin," MedChemComm, 2012, 3:494-497.
Florindo et al., "Evaluation of solubility and partition properties of ampicillin-based ionic liquids," International Journal of Pharmaceutics, 2013, 456: 553-559.
Garwicz et al., Biosynthetic profiles of neutrophil serine proteases in a human bone marrow derived cellular myeloid differentiation model, Haematologica, 2005, 90:38-44.
Gullberg et al., "Carboxyl-terminal prodomain-deleted human leukocyte elastase and cathepsin Gare efficiently targeted to granules and enzymatically activated in the rat basophilic/mast cell line RBL," J. Biol. Chem., 1995, 270:12912-12918.
Holmes et al., "Utility of genetic determinants of lipids and cardiovascular events in assessing risk," Nat. Rev. Cardiol., 2011, 8:207-221.
International Search Report and Written Opinion in International Application No. PCT/US2018/014258, mailed on Sep. 10, 2018, 25 pages.
Janciauskiene et al., "C-terminal fragment of [alpha]1-antitrypsin activates human monocytes to a pro-inflammatory state through interactions with the CD36 scavenger receptor and LDL receptor," Atherosclerosis, 2001, 158:41-51.
Jayashankar et al., "Human Leukocyte Elastase Inhibitors: Analog Based Studies to Design Novel Lead Compounds for the Treatment of COPD," Journal of Biomedical Science and Research, Jan. 2010, 2: 60-72.
Kindzelskii and Petty, "Intracellular Calcium Waves Accompany Neutrophil Polarization, Formylmethionylleucylphenylalanine Stimulation, and Phagocytosis: A High Speed Microscopy Study," J. Immunol., 2003, 170:64-72.
Kounnas et al., "Cellular internalization and degradation of antithrombin III-thrombin, heparin cofactor II-thrombin, and alpha 1-antitrypsin-trypsin complexes is mediated by the low density lipoprotein receptor-related protein," J. Biol. Chem., 271:6523-6529.
Lapidot and Petit, "Current understanding of stem cell mobilization: The roles of chemokines, proteolytic enzymes, adhesion molecules, cytokines, and stromal cells," Exp. Hematol., 2002, 30: 973-981.
Levingston and Young, "Transient immunological and clinical effectiveness of treating mice bearing premalignant oral lesions with PD-I antibodies," Int. J. Cancer, 2017, 140:1609-1619.
Mashiba et al., "In Vivo complex formation of oxidized al-antitrypsin and LDL," Arterioscler. Thromb. Vase. Biol., 2001, 21:1801-1808.
Messmer et al., "Endogenously expressed nefuncouples cytokine and chemokine production from membrane phenotypic maturation in dendritic cells," J. Immunol., 2002, 169:4172-4182.
Modarresi et al., "WNT/β-Catenin Signaling is Involved in Regulation of Osteoclast Differentiation by Human Immunodeficiency Virus Protease Inhibitor Ritonavir: Relationship to Human Immunodeficiency Virus-Linked Bone Mineral Loss, " Am. J. Pathol., 2009, 174:123-135.
Navia et al., "Crystallographic study of a -lactam inhibitor complex with elastase at 1.84Å resolution," Nature, May 1987, 327:79-82.
Nour et al., "Effect of Garamycin and Cefobid on liver function of hyperlipidemic rats," Journal of Drug Research, 2000, 23: 263-276 (abstract only).
Office Action in Israel Appln. No. 268155, dated Dec. 5, 2021, 758 pages (with English translation).
Paulekuhn et al., "Trends in Active Pharmaceutical Ingredient Salt Selection based on Analysis of the Orange Book Database," J. Med. Chem., 2007, 50:6665-6672.
Stalenhoef et al., "Metabolism of apolipoproteins B-48 and B-100 of triglyceride-rich lipoproteins in normal and lipoprotein lipase-deficient humans," PNAS, 1984, 81:1839-1843.

(56) References Cited

OTHER PUBLICATIONS

Tavor et al., "Motility, proliferation, and egress to the circulation of human AML cells are elastase dependent in NOD/SCID chimeric mice," Blood, 2005, 106:2120-2127.

Turnidge and Paterson, "Setting and Revising Antibacterial Susceptibility Breakpoints," Clin. Microbiol. Rev., 2007, 20:391-408.

Tyagi, "Reversible inhibition of neutrophil elastase by thiol-modified al-protease inhibitor," J. Biol. Chem., 1991, 266:5279-5285.

Veniant et al., "Lipoprotein clearance mechanisms in LDL receptordeficient "Apo-B48-only" and "Apo-B 100-only" mice, " J. Clin. Invest., 1998, 102:1559-1568.

Wang et al., "[Cefodizime increases peripheral blood CD4/CD8 and Thl/Th2 ratios in senile patients with bacterial pneumonia]," Xi Bao Yu Fen Zi Mian Yi Xue Za Zhi, Apr. 2015, 31: 528-31 (abstract only) Retrieved from: https://www.ncbi.nlm.nih.gov/pubmed/25854575, 2 pages.

Wolf et al., "Amoeboid shape change and contact guidance: T-lymphocyte crawling through fibrilar collagen is independent of matrix remodeling by MMPs and other proteases," Blood, 2003, 102:3262-3269.

Wright et al., "Phorbol esters cause sequential activation and deactivation of complement receptors on polymorphonuclear leukocytes," J. Immunol., 1986, 136:1759-1764.

Adherence to glass in response to chemokines and serine proteinase inhibitors.

Mueller-Hinton agar plates comparing the antibiotic activities of D-ampicillin with the antibiotic activities of L-ampicillin.

Stimulation of cell migration and endocytosis induced by L-ampicillin. Receptor Polarization.

Changes in lipoprotein levels in mice on a high fat diet.

Changes in CD3+ T lymphocyte levels and T progenitor cells in mice treated with L-ampicillin.

L-ampicillin (Alpha 101) in combination with anti-PD-1 cures mice of renal cell carcinoma.

D-ampicillin (CAS no. 69-53-4)

(2S,5R,6R)-6-{[(2R)-2-Amino-2-phenylacetyl]amino}-3,3-dimethyl-7-oxo-4-thia-1-azabicyclo[3.2.0]heptane-2-carboxylic acid)

L-ampicillin (CAS no. 19379-33-0)

(2S,5R,6R)-6-{[(2S)-2-Amino-2-phenylacetyl]amino}-3,3-dimethyl-7-oxo-4-thia-1-azabicyclo[3.2.0]heptane-2-carboxylic acid)

Absolute configuration of D-ampicillin and L-ampicillin.

Reaction of phenylamine carboxylic acid with benzyl carbonochloridate in synthesis of the tromethamine salt of L-ampicillan Reaction of ethyl chloroformate and triethylamine with 6-aminopenicillic acid in the synthesis of the tromethamine salt of L-amplicillin Reaction with compound 3 and THF in the synthesis of the tromethamine salt of L-ampicillin Reaction of compound 4 with 1M C4H11NO in the synthesis of the tromethamine salt of L-ampicillin

THERAPEUTIC USE OF LEVOROTATORY β-LACTAMS IN HEMATOPOIESIS, IMMUNO-ONCOLOGY THERAPY, AND REGULATION OF LIPOPROTEIN AND APOLIPOPROTEIN LEVELS

CROSS REFERENCE TO RELATED APPLICATIONS

This application is a continuation of U.S. patent application Ser. No. 16/925,811 filed Jul. 10, 2020, which is a divisional of U.S. patent application Ser. No. 16/544,774, filed Aug. 19, 2019 now U.S. Pat. No. 10,709,693, which is a divisional of U.S. patent application Ser. No. 15/874,694, filed Jan. 18, 2018, now U.S. Pat. No. 10,413,530, which claims the benefit of U.S. provisional Patent Application 62/447,689, filed Jan. 18, 2017, which is hereby incorporated by reference in its entirety.

TECHNICAL FIELD

This present invention relates to the use of levorotatory β-lactams in hematopoiesis, immune-oncology therapy, and the regulation of lipoprotein and apolipoprotein levels.

BACKGROUND OF THE INVENTION

Human leukocyte elastase (HLE, EC.3.4.21.37) is a serine proteinase that is synthesized and processed as a single molecular protein that is targeted exclusively for the cell surface (HLE-CS) early in ontogeny of lymphoid and myeloid cells when they are too immature to form granules. However, HLE is targeted for granule compartmentalization (HLE-G) later in ontogeny when cells develop the capability to form granules (Gullberg et al., 1995; Garwicz et al., 2005). Whereas HLE-G has enzymatic activity, HLE-CS acts as a receptor, and there is no evidence of its having enzymatic activity.

The primary physiologic mechanism for controlling the enzymatic activity of HLE-G is the abundant proteinase inhibitor alpha-1 proteinase inhibitor (α1PI, α1 antitrypsin). When bound to HLE-G, a covalent-like complex is formed in which neither α1PI, nor HLE-G are cleaved (Dementiev et al., 2006). Similarly, when α1PI binds to HLE-CS, a complex is formed which does not appear to involve completion of enzymatic activity, and the complex induces polarization of functionally-related receptors and cell motility (Wolf et al., 2003). Functionally-related receptors include the chemokine receptor CXCR4 (CD184), CD4, and the T cell antigen receptor (TcR).

In healthy individuals, 98% of α1PI is in the active form. Normal ranges are 18-53 µM active and 0-11 µM inactive α1PI (Bristow et al., 2001). Active α1PI circulates in blood in two isoforms in dynamic equilibrium: 1) native α1PI, which binds irreversibly to HLE-CS, and 2) thiol-modified α1PI, which binds reversibly to HLE-CS (Tyagi, 1991).

Inactive α1PI arises during infection or inflammation via modification of active α1PI by factors released from microorganisms or host cells. Inactive α1PI can arise by complexing with HLE-G or HLE-CS, being cleaved by proteinases other than HLE, or oxygenation. In its inactivated form, α1PI binds to low density lipoprotein (LDL), apoB, and members of the LDL receptor family (LDL-RFMs), whereby α1PI facilitates LDL uptake into cells (Mashiba et al., 2001; Janciauskiene et al., 2001).

Binding of active α1PI to HLE-CS at the leading edge of migrating cells induces aggregation and polarization of LDL-RFMs with other functionally-related receptors (Bristow et al., 2003; 2008; Bristow and Flood, 1993). Cellular locomotion repositions the HLE-CS complex including functionally-associated receptors to the trailing edge of the cell where LDL-RFMs on the same cell bind to the α1PI-HLE-CS complexes through an interaction that involves the α1PI C-terminal domain (C-36, VIRIP) (Kounnas et al., 1996; Janciauskiene el al., 2001). This interaction induces internalization (endocytosis) of LDL-RFMs including functionally-related receptors within the aggregate and entities bound to them such as lipoproteins and viruses. This action furthers retraction of the trailing edge of the migrating cell thereby promoting forward locomotion (Kounnas el al., 1996; Cao el al., 2006; Bristow et al., 2003; Bristow et al., 2013).

The recycling of endocytosed receptors and polarization at the leading edge of a migrating cells followed by endocytosis at the trailing edge operates somewhat like a conveyor belt. If one of the components involved in this conveyor belt mechanism is missing or blocked, the cell halts migrating. For example, bacteria, snake bites, blood clotting, and most other non-normal situations produce non-normal proteases which cleave sentinel proteinase inhibitors including α1PI. When α1PI is inactivated, it can no longer bind its receptor HLE-CS. In the absence of α1PI-HLE-CS complexes, the LDL-RFMs are not triggered for endocytosis and this causes blood cells to stop migrating. This mechanistic process provides a method for locomoting immune cells to sample the environment for nutrients (e.g. lipoproteins and insulin-coupled glucose), toxic material (e.g. viruses, bacterial enzymes, inflammatory products), or inert material (e.g. recycled receptors). Due to the dynamics of the process, targeting HLE-CS using levorotatory β-lactams allows regulation of hematopoiesis, lipoprotein levels, and unwanted tissue degradation.

Cell motility results from selective and sequential adherence and release produced by activation and deactivation of receptors (Wright and Meyer, 1986; Ali et al., 1996), consequent polar segregation of related membrane proteins to the leading edge or trailing uropod, and both clockwise and counterclockwise propagation of Ca++ waves which initiate from different locations in the cell (Kindzelskii and Petty, 2003). Thus, several aspects of the complex process may be quantitated. The most direct and most easily interpreted method for quantitating cell motility is the enumeration of adherent cells in response to a chemotactic agent such as α1PI.

Applicant's co-pending U.S. patent application Ser. No. 13/302,821 is directed to a method for increasing the number of circulating CD4+ T-lymphocytes in subjects receiving antiretroviral therapy comprising administering to a subject in need of such treatment an amount of active α1PI effective to increase the number of circulating CD4+T-lymphocytes in the subject.

Applicant's co-pending Ser. No. 13/948,446 is directed to a method of modulating LDL levels, HDL levels, cholesterol levels, and triglyceride levels in a subject comprising administering to the subject in need of such treatment a pharmaceutical composition comprising a therapeutically effective amount of active α1PI, thereby modulating the distribution of LDL levels, HDL levels, cholesterol levels, and triglyceride levels in the subject.

The hematopoietic role of α1PI has not been therapeutically exploited thus far. Its use has been limited due to its high cost and short supply. Previous therapeutic applications of α1PI have been restricted to augmentation for the purpose of ameliorating respiratory distress such as occurs in emphysema and chronic obstructive pulmonary disease (COPD) in patients diagnosed with inherited α1PI deficiency. Commercially, α1PI is available from a few sources including PROLASTIN®-C, (Grifols Therapeutics Inc., Research Triangle Park, N.C.) and ZEMAIRA® (CSL Behring LLC, King of Prussia, Pa.) as a cryoprecipitate preparation isolated from human plasma.

What is needed in the art are small molecules to act as surrogates for α1PI. The present invention provides such small molecule compounds useful in arresting degradative enzymatic activity for the treatment of respiratory distress such as occurs in emphysema and COPD, modulating lipoprotein and apolipoprotein levels, and for regulating the number of circulating CD4+ or CD8+ T-lymphocytes (CD4/CD8 ratio) in subjects in need of such treatment.

SUMMARY OF THE INVENTION

It has now been unexpectedly discovered that all 5 classes of β-lactam antibiotics, including L-ampicillin, bind to soluble granule-associated elastase (HLE-G) and to cell surface elastase (HLE-CS), induce receptor polarization and stimulate cell motility. As these are the biological activities of α1PI, β-lactams can be used as a surrogate for α1PI in binding to HLE-CS thereby modulating lipoprotein and apolipoprotein levels and regulating the number of circulating CD4+ or CD8+ T-lymphocytes (CD4/CD8 ratio) in human subjects, as well as arresting degradative enzymatic activity for the treatment of respiratory distress such as occurs in emphysema and chronic obstructive pulmonary disease (COPD). Further, some β-lactams such as L-ampicillin can be immune enhancing whereas others such as Cephelaxin can be immune suppressing. Most drugs that target cells, including α1PI, exhibit a bell shaped curve where a high dose or high affinity is as ineffective as a low dose or low affinity, and the optimal dose of each drug is somewhere in between.

In one embodiment, the present invention provides a method for increasing the CD4/CD8 ratio by increasing the number of CD4+ T-lymphocytes or decreasing the number of CD8+ lymphocytes in the serum of a subject in need of such treatment comprising, administering to the subject a pharmaceutical composition comprising an amount of a levorotatory β-lactam such as L-ampicillin effective to increase the CD4/CD8 ratio in said patient's serum.

In another embodiment, the present invention provides a method for decreasing the CD4/CD8 ratio by decreasing the number of CD4+ T-lymphocytes or increasing the number of CD8+ lymphocytes in the serum of a subject in need of such treatment comprising, administering to the subject a pharmaceutical composition comprising an amount of a levorotatory β-lactam such as L-cephalexin effective to decrease the CD4/CD8 ratio in said patient's serum.

In another embodiment, the method further comprises the step of determining the CD4/CD8 ratio, the number of CD4+ T-lymphocytes and the number of CD8+ lymphocytes in said patient's serum.

In a further embodiment the β-lactam is selected from a group consisting of Cephems.

In a further embodiment, the β-lactam is selected from a group consisting of Penams.

In a further embodiment, the β-lactam is selected from a group consisting of Monobactams.

In a further embodiment, the β-lactam is selected from a group consisting of Penems.

In a further embodiment, the β-lactam is selected from a group consisting of Carbapenems.

In a still further embodiment, the subject is suffering from secondary immune deficiency, such as occurs in malnutrition or HIV-1 disease or in cancer therapy.

In a still further embodiment, the subject is suffering from cancer and is being treated with immune checkpoint inhibitors.

In a still further embodiment, the subject is suffering from immune hyperactivation such as occurs in autoimmunity or graft-versus-host disease.

In another embodiment, the subject is suffering from inherited α1PI deficiency.

In another embodiment, the CD4/CD8 ratio or the number of CD4+ T-lymphocytes in the subject is undesirably low.

In another embodiment, the CD4/CD8 ratio or the number of CD4+ T lymphocytes in the subject is undesirably high, requiring immune suppression therapy.

In another embodiment, the subject is a patient suffering from a solid tumor including but not limited to melanoma, renal cell carcinoma, non-small cell lung cancer, bladder cancer, cervical cancer, gastric cancer, liver cancer, pancreatic cancer, and brain cancer.

In another embodiment, the subject is a patient exposed to environmental toxins such as radiation or chemotherapy.

In another embodiment, the subject is suffering from at least one condition selected from the group consisting of viral infection, bacterial infection, and malnutrition.

In another embodiment, the subject is suffering from an autoimmune disease.

In another embodiment, the subject is suffering from graft-versus-host disease.

In a further embodiment, the present invention provides a method for modulating LDL levels, HDL levels, cholesterol levels, and other lipoprotein and apolipoprotein levels derived from or resulting from dietary fats, LDL, HDL and cholesterol and other lipoproteins and apolipoproteins in a subject comprising administering to a subject in need of such treatment a pharmaceutical composition comprising a therapeutically effective amount of a β-lactam thereby modulating LDL levels, HDL levels, cholesterol levels, and the levels of other lipoproteins and apolipoproteins derived from or resulting from dietary fats, LDL, HDL, cholesterol, and other lipoproteins and apolipoproteins in the subject.

In another embodiment, the method further comprises determining LDL levels, HDL levels, cholesterol levels, and the levels of other lipoproteins and apolipoproteins derived from or resulting from dietary fats, LDL, HDL cholesterol, and other lipoproteins and apolipoproteins in said subject's serum before administration of the β-lactam.

In another embodiment, the method further comprises determining LDL levels, HDL levels, cholesterol levels, and the levels of other lipoproteins and apolipoproteins resulting from or derived from dietary fats, LDL, HDL, cholesterol, and other lipoproteins and apolipoproteins in said subject's serum after administration of the β-Lactam.

In yet another embodiment, modulation comprises lowering LDL levels and the levels of lipoproteins and apolipoproteins resulting from or derived from LDL.

In another embodiment, modulation comprises increasing HDL levels and the levels of lipoproteins and apolipoproteins resulting from or derived from HDL.

In another embodiment, modulation comprises modulating apoB48 or apoB100 levels and the levels of lipoproteins and apolipoproteins resulting from or derived from apoB48 or apoB100.

In another embodiment, the subject is a human or a non-human animal.

In another embodiment, an LDL inhibitor or cholesterol lowering drug is selected from the group consisting of statins, PCSK9 inhibitors, fibrate, niacin, and bile acid sequestrant is administered to the subject.

In a particularly preferred embodiment the β-lactam is an L-ampicillin salt.

In another preferred embodiment the levels of LDL and the levels of other lipoproteins and apolipoproteins resulting from or derived from LDL are lowered.

In another preferred embodiment the levels of HDL and the levels of other lipoproteins and apolipoproteins resulting from or derived from HDL are increased.

In a still further embodiment the present invention provides a method for treating patients suffering from congenital α1PI deficiency and suffering from COPD comprising administering to said patients an effective amount of a β-lactam.

In yet another embodiment the present invention provides a composition of matter comprising the tromethamine salt of L-ampicillin.

In another embodiment the present invention provides a pharmaceutical composition comprising the tromethamine salt of L-ampicillin and a pharmaceutically acceptable carrier, excipient, or diluent.

In a still further embodiment the present invention provides a method for treating patients suffering from congenital α1PI deficiency and suffering from COPD comprising administering to said patients an effective amount of a β-lactam.

In a further embodiment, the present invention provides a method for treating a patient suffering from respiratory distress caused by emphysema and COPD comprising administering to a patient in need of such treatment of a therapeutically effective amount a β-Lactam.

The details of one or more embodiments of the invention are set forth in the accompanying drawings and the description below. Other features, objects, and advantages of the invention will be apparent from the present description, drawings, and claims.

BRIEF DESCRIPTION OF DRAWINGS

FIG. 1A depicts adherent cells enumerated in response to chemokines CXCL12α(●), CCL3 (■), CCL4 (▲), and CCL5 (▼) or in response to proteinase inhibitors α1PI (▲), antithrombin III (ATIII) (■), and anti-chymotryspin ($\alpha_1$ACT); FIG. 1B depicts that HIV permissive (plus) clone 10 (●), but not HIV non-permissive (minus) clone 17 (■), was stimulated to adhere by MAAPVCK, a synthetic peptide inhibitor for HLE and by TPCK, a synthetic peptide inhibitor for chymotrypsin. Plus clone 10 (●), but not minus clone 17 (■), was stimulated to adhere in response to the HIV fusion peptide (FLGFL). Neither subclone was influenced by the thrombin agonist peptide (SFLLRN). Two different preparations of $\alpha_1$PI were determined to be 32.7% (●) and 8.3% active (■); FIG. 1C depicts Plus clone 10 stimulated by these two $\alpha_1$PI preparations responded to equivalent optimal concentrations of active $\alpha_1$PI, but different concentrations of inactive $\alpha_1$PI.

DETAILED DESCRIPTION

Definitions

Figure 1A:
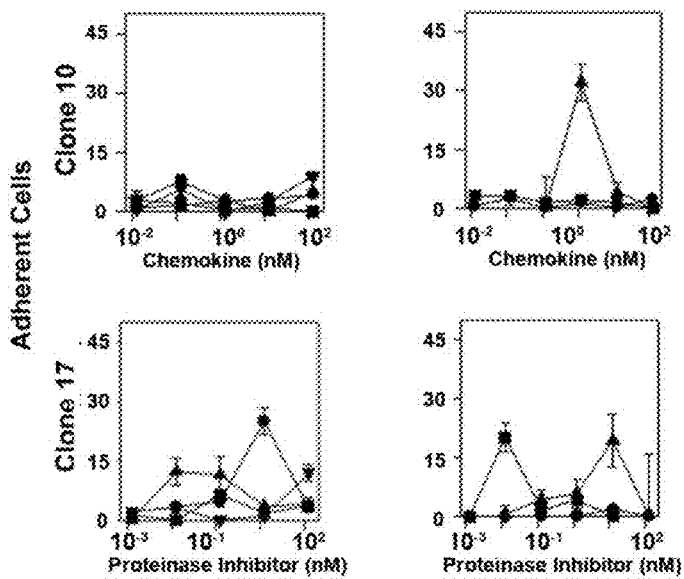
FIG. 1A-1C are graphs demonstrating that binding to HLE-CS inhibits chemokine-induced locomotion of human leukemic cells and enhances locomotion of human stem cells.

The term "about" or "approximately" usually means within an acceptable error range for the type of value and method of measurement. For example, it can mean within 20%, more preferably within 10%, and most preferably still within 5% of a given value or range. Alternatively, especially in biological systems, the term "about" means within about a log (i.e., an order of magnitude) preferably within a factor of two of a given value.

"Active α1PI" is the fraction of full length, unmodified α1PI in plasma or other fluids that has the capacity to inhibit elastase activity.

"Inactive α1PI" is the fraction of α1PI in plasma or other fluids that does not have the capacity to inhibit elastase activity. Active α1PI may be inactivated by proteolytic cleavage, proteinase complexing, antibody complexing, or oxidation.

"β-lactam antibiotics" are defined herein as members of the group consisting of Cephalosporins (Cephems); Penicillins (Penams); Monobactams; Penems and Carbapenems.

"Substantially no bactericidal activity" as used herein in reference to L-ampicillin is defined by the 2014 Clinical & Laboratory Standards Institute (CLSI) criteria as a 4-fold dosage difference for ampicillin-resistant vs susceptible *E. coli* (Table 2A of the 2014 CLSI M100-S24) (CLSI, 2014). Because the dosage difference between D-ampicillin and L-ampicillin is 10-fold, L-ampicillin is not considered to be an effective antibiotic.

The terms "decrease", "decreased", "reduced", "reduction" or "down-regulated" are all used herein generally to mean a decrease by a statistically significant amount. However, for avoidance of doubt, "reduced", "reduction", "down-regulated" "decreased" or "decrease" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold decrease, or any decrease between 1.0-fold and 10-fold or greater as compared to a reference level.

The terms "increased", "increase" or "up-regulated" are all used herein to generally mean an increase by a statistically significant amount; for the avoidance of any doubt, the terms "increased" or "increase" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 0.5-fold, or at least about a 1.0-fold, or at least about a 1.2-fold, or at least about a 1.5-fold, or at least about a 2-fold, or at least about a 3-fold, or at least about a 4-fold, or at least about a 5-fold or at least about a 10-fold increase, or any increase between 1.0-fold and 10-fold or greater as compared to a reference level.

As used herein, "modulate" or "modulating" refers to increase or decrease, or an increase or a decrease, for example an increase in the level of HDL or a decrease in the level of LDL or an increase in the number of immune cells, or a decrease in the number of immune cells.

Non-limiting examples of lipoproteins and apolipoproteins derived from HDL, LDL and cholesterol include chylomicrons, lipoprotein(s), intermediate density lipoproteins (IDL), very low density lipoproteins (VLDL), and apolipoproteins (apo) including apolipoproteins A, B, C, D, E, H, and L, and their molecular variants including apoA-I, apoA-II, apoA-IV, apoA-V, apoB48, apoB100, apoC-I, apoC-II, apoC-III, and apoC-IV. Exchangeable apolipoproteins (apoA, apoC and apoE) have the same genomic structure and are members of a multi-gene family that evolved from a common ancestral gene. ApoA1 and ApoA4 are part of the APOA1/C3/A4/A5 gene cluster on chromosome 11. Hundreds of genetic polymorphisms of the apolipoproteins have been described, and many of them alter their structure and function as disclosed in Holmes et al, 2011.

A "level", in some embodiments, may itself be a relative level that reflects a comparison of levels between two states. Relative levels that reflect a comparison (e.g., ratio, difference, logarithmic difference, percentage change, etc.) between two states (e.g., healthy and diseased). The use of relative levels is beneficial in some cases because, to an extent, they exclude measurement related variations (e.g., laboratory personnel, laboratories, measurements devices, reagent lots/preparations, assay kits, etc.). However, the invention is not so limited.

As used herein the terms "therapeutically effective" and "effective amount", used interchangeably, apply to a dose or amount refer to a quantity of a composition, compound or pharmaceutical formulation that is sufficient to result in a desired activity upon administration to an animal in need thereof. Within the context of the present invention, the term "therapeutically effective" refers to that quantity of a composition, compound or pharmaceutical formulation that is sufficient to reduce or eliminate at least one symptom of a disease or condition specified herein. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level.

Pharmaceutical compositions include an active agent, i.e., a β-lactam and a pharmaceutically acceptable carrier, excipient, or diluent.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

When formulated in a pharmaceutical composition, a therapeutic compound of the present invention can be admixed with a pharmaceutically acceptable carrier or excipient. As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human.

The term "pharmaceutically acceptable derivative" as used herein means any pharmaceutically acceptable salt, solvate or prodrug, e.g. ester, of a compound of the invention, which upon administration to the recipient is capable of providing (directly or indirectly) a compound of the invention, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Preferred pharmaceutically acceptable derivatives are salts, solvates, esters, carbamates, and phosphate esters. Particularly preferred pharmaceutically acceptable derivatives are salts, solvates, and esters. Most preferred pharmaceutically acceptable derivatives are salts and esters.

All classes of β-lactams contain proton donating groups, e.g. carboxylic acid or hydrofluoric acid, allowing them to be easily transformed into pharmaceutically acceptable salts. Non-limiting examples of pharmaceutically acceptable salts may be formed with cations including benzathine, calcium, cholinate, diethanolamine, diethylamine, lysine, magnesium, meglumine, piperazine, potassium, procaine, silver, sodium, tromethamine, or zinc. Further, nonlimiting examples of pharmaceutically acceptable salts may be formed with anions including acetate, benzoate, besylate, bromide, camphorsulfonate, chloride, chlortheophyllinate, citrate, ethandisulfonate, fumarate, gluceptate, gluconate, glucuronate, hippurate, iodide, isethionate, lactate, lactobionate, laurylsulfate, malate, maleate, mesylate, methyl sulfate, naphthoate, napsylate, nitrate, octadecenoate, oleate, oxalate, pamoate, phosphate, polygalacturonate, succinate, sulfate, sulfosalicylate, tartrate, tosylate, or trifluoroacetate (Paulekuhn et al., 2007).

While it is possible to use a composition provided by the present invention for therapy as is, it may be preferable to administer it in a pharmaceutical formulation, e.g., in admixture with a suitable pharmaceutical excipient, diluent, or carrier selected with regard to the intended route of administration and standard pharmaceutical practice. Accordingly, in one aspect, the present invention provides a pharmaceutical composition or formulation comprising at least one active composition, or a pharmaceutically acceptable derivative thereof, in association with a pharmaceutically acceptable excipient, diluent, and/or carrier. The excipient, diluent and/or carrier must be "acceptable" in the sense of being compatible with the other ingredients of the formulation and not deleterious to the recipient thereof.

In a particularly preferred embodiment the β-lactam is the tromethamine salt of L-ampicillin prepared using tromethamine (hydroxymethyl)aminomethane, CAS no. 77-86-1) and producing (tromethamine; (2S,5R,6R)-6-{[(2S)-2-Amino-2-phenylacetyl] amino}-3,3-dimethyl-7-oxo-4-thia-1-azabicyclo[3.2.0]heptane-2-carboxylic acid). L-ampicillin tromethamine salt is a diastereomer of D-ampicillin sodium salt (sodium; (2S,5R,6R)-6-[[(2R)-2-amino-2-phenylacetyl] amino]-3,3-dimethyl-7-oxo-4-thia-1-azabicyclo[3.2.0]heptane-2-carboxylate). While L-ampicillin tromethamine salts have not been reported in the scientific literature, their structure has been confirmed by the inventors by nuclear magnetic resonance proton and carbon analysis using a Bruker Ascend™ 700 MHz spectrometer.

Because L-ampicillin and D-ampicillin are produced synthetically or semi-synthetically using chiral starting materials, they are not found as racemic mixtures (Example 6). L-ampicillin is soluble in tromethamine at pH 8.6 and is not soluble in 100% denatured ethanol whereas D-ampicillin is poorly soluble in tromethamine, at pH 8.6 and is soluble at 6133 g/L water as well as in 100% denatured ethanol (demonstrated experimentally by the inventors and disclosed in Bartzatt et al., 2007).

The compositions or pharmaceutical formulations of the invention can be formulated for administration in any convenient way for use in human or veterinary medicine.

For human therapy, the pharmaceutical formulations or compositions, including each of the active agents, are prepared in accordance with good manufacturing process (GMP) standards, as set by the Food & Drug Administration (FDA). Quality assurance (QA) and quality control (QC) standards will include testing for purity and function and other standard measures.

Although there is extensive knowledge about treating inflammation and regulating the reactivity of the immune system, for patients with secondary immune deficiency there are only 2 FDA approved therapeutic options, gamma globulin infusion and bone marrow transplantation. Both of these options are painful, have serious safety issues, and offer limited efficacy. Every patient with cancer-treatment induced immune deficiency, every HIV-infected patient, every patient with other virus- or environmentally-induced immune deficiency, suffers because of the lack of a therapeutic agent to treat secondary immune deficiency.

The present inventors previously discovered that the human protein α1PI is both safe and effective in restoring the immune system in patients with secondary immune deficiency by binding to its cell surface receptor, HLE-CS. While the use of α1PI for treating the large number of patients with secondary immune deficiency is not economically feasible due to supply and cost issues, synthetic drugs that mimic the biological activity of α1PI by binding to HLE-CS are needed in the art.

Disclosed herein is surprising and unexpected discovery that L-isomers of β-lactams, including the salts of the L-isomer of D-ampicillin (hereinafter "L-ampicillin"), which have substantially no bactericidal activity (as defined herein), have the biological properties of active α1PI required for their use as surrogates for α1PI for the purposes of:

(1) Ameliorating respiratory distress such as occurs in emphysema and chronic obstructive pulmonary disease (COPD) in patients suffering from congenital α1PI deficiency;

(2) Treating patients suffering from immune dysfunction by inducing mobilization of lymphoid-committed progenitor cells from hematopoietic tissue. This produces elevated levels of circulating T-lymphocytes in individuals in need of such treatment due to cancer, atherosclerosis, autoimmunity, stem cell transplantation, organ transplantation, HIV-1 infection, microbial infection, leukemia, and other diseases affected by cells of the immune system.

(3) Treating patients suffering from hyperlipidemia by regulating lipoprotein and apolipoprotein levels, for example, HDL and LDL and cholesterol levels and other lipoproteins and apolipoproteins derived from dietary fats, HDL and LDL and cholesterol as a consequence of its ability to elevate T-lymphocytes which transport lipoproteins and apolipoproteins throughout the tissues.

(4) Treating cancer patients suffering from tumors.

(5) Treating cancer patients suffering from tumors in combination with immune checkpoint inhibitors.

It is surprising and unexpected that small molecules such as levorotatory β-lactams have the biological properties of active α1PI and can be used as surrogates in the above-described methods.

L-ampicillin and salts thereof are particularly preferred for use in the present invention because as shown below in Example 3, L-ampicillin has substantially no anti-bactericidal activity as defined herein.

Functional Capacity of L-Ampicillin and Other Levorotatory β-Lactams of the Present Invention Pursuant to the present invention, L-ampicillin ((2S,5R,6R)-6-((S)-2-amino-2 phenylacetamcido)-3,3-dimethyl-7-oxo-4-thia-1-azabicyclo[3.2.0] heptane-2-acid, CAS #19379-33-0) and other β-lactams can be used as surrogates for α1PI in the methods described herein. The present inventors discovered that L-ampicillin binds to soluble and cell surface elastase and modulates lipoprotein and apolipoprotein levels, induces receptor polarization, stimulates cell motility, and increases the number of CD4+ T-lymphocytes in the serum of a subject in need of such treatment.

Based on these properties, L-ampicillin and other levorotatory β-lactams can be used in a method for regulating the number of CD4+ T-lymphocytes in the serum of a subject in need of such treatment, modulating LDL levels, HDL levels, cholesterol levels, and the levels of other lipoproteins and apolipoproteins resulting from or derived from LDL, HDL, cholesterol, and other lipoproteins and apolipoproteins in a subject including patients suffering from congenital α1PI deficiency.

As set forth in Example 2 below, β-lactams bind to and inactivate soluble elastase:

The procedures for measuring the capacity of substances to inhibit soluble forms of elastase or HLE-G are well known to those of ordinary skill in the art (U.S. Pat. No. 6,887,678; Bristow et al., 1998). Briefly, soluble human leukocyte elastase (HLE-G) is incubated for 2 minutes with a test substance, and to this mixture is added the elastase substrate succinic-L-Ala-L-Ala-L-Ala-p-nitroanilide (SA3NA, Sigma-Aldrich). Results are detected by measuring the color change at 405 nm. IC50 is calculated from these results.

As set forth in Example 4 below, L-ampicillin induces receptor polarization and stimulates cell motility.

The procedures for inducing receptor polarization have been described (Bristow et al., 2003). The cells of interest (monocytes, lymphocytes, neutrophils, or other blood cells, e.g. leukemic cells) are isolated from blood or tissue using standard techniques (for example, as disclosed in Messmer et al., 2002) and examined for reactivity with L-ampicillin.

To examine receptor polarization, microscope slides are prepared by adding serial dilutions of a β-lactams. Cells are added to the microscope slides and incubated for 30 minutes in humidified 5% $CO_2$ at 37° C. Unattached cells are removed by washing, and attached cells are fixed by application of 4% paraformaldehyde after which attached cells are counted by light microscopy and photographed using confocal microscopy As demonstrated in Example 4 below, L-ampicillin stimulates cell motility. Confocal microscopy was used to demonstrate that the cells treated with L-ampicillin exhibited the morphology of cells undergoing cell motility.

To demonstrate that L-ampicillin mobilizes lymphoid-committed progenitor cells, the Jackson Laboratory C57BL/6 Diet-Induced Obesity (DIO) diabetic mouse model is used. The DIO mouse model is used to assess the capacity of L-ampicillin to mobilize lymphoid- or myeloid-lineage cells and lower LDL levels.

Therapeutically Effective Amounts of Levorotatory 13-Lactams for Use in the Present Invention According to the manufacturer, the recommended regimen for PROLASTIN-C® (human α1PI) for treating α1PI deficiency is repeated weekly infusions of 60 mg/kg at a rate of 0.08 ml/kg/minute. The specific activity of PROLASTIN-C® is 70%, wherein specific activity is defined as the inhibition of elastase activity as described in the package insert. Thus, the recommended dose of α1PI is 42 mg/kg of active α1PI to achieve half the normal level of α1PI and 84 mg/kg or 1.53 millimol/kg to achieve a normal level of α1PI. Since L-ampicillin has a mass of 349.41 mg/mole, 1.53 millimol/kg is 0.53 mg/kg is the target dose of L-ampicillin. By comparison, the pediatric dose of D-ampicillin for treating bacterial infections is 50-100 mg/kg/day (every 6 hr.), and pediatric blood volume is 70 ml/kg; thus the pediatric dose of D-ampicillin is 50-100 mg/70 ml which is equivalent to 2-4 millimol/day or 0.7-1.3 millimol every 6 hr (q6 hr). The commonly used adult dose is 750-1500 mg/day (q6 hr), and adult blood volume is 5 L which is equivalent to 0.4-0.9 millimol/day or 0.2-0.3 millimol q6 hr. Thus, the commonly used doses of D-ampicillin are approximately equivalent to the therapeutically effective doses of L-ampicillin. Whereas α1PI treatment is given weekly by infusion, L-ampicillin can be administered orally and more frequently, if necessary.

In one preferred embodiment, the therapeutically effective amounts of levorotatory β-lactams for use in this embodiment of the present invention will be between about 100 mg and about 3000 mg/kg body weight administered 4 times per day (qid) for adults and between about 10 mg and 200 mg/kg qid for pediatrics.

The preferred route of administration for levorotatory β-lactams is oral but other routes, such as subcutaneous injection, intramuscular injection, and topical administration can be used.

L-ampicillin for use in the present invention is commercially available from multiple sources including BOC Sciences, Shirley, N.Y. L-ampicillin and the salt of L-ampicillin can be chemically synthesized using, for example, the method described in Example 6 below. Commercial sources for other β-lactams for use in the present invention are set forth in Example 9 below.

Treatment Outcome Measurements:

To determine whether treatment affects soluble elastase inhibitory activity, individuals are monitored weekly for changes in the active and inactive α1PI blood levels (Bristow et al., 1998) (U.S. Pat. No. 6,887,678). Briefly, a constant amount of active site-titrated elastase is allowed to incubate with serial dilutions of serum for 2 minutes at 37° C. after which an elastase substrate is added. Determination of the molecules of substrate cleaved by residual, uninhibited elastase is used to calculate the molecules of active and inactive α1PI in blood. Changes in measurements of active and inactive α1PI activity are followed up with determination of whether the changes are due to physiological changes or interference in measuring active and inactive α1PI due to the presence of the β-lactam in blood. For patients receiving β-lactam treatment, active and inactive α1PI are measured before, during, and after treatment.

To determine the effectiveness of treatment on inducing changes in levels of targeted blood cell populations, treated individuals are monitored weekly for changes in complete blood count and differential, as well as for changes in specific subsets of blood cells such as CD4+ lymphocyte cells and HLE-CS+ cells using flow cytometry (Bristow et al., 2001; Bristow, 2001; U.S. Pat. No. 6,858,400). Briefly, 100 μl of whole blood is incubated with a panel of fluorescently-labeled monoclonal antibodies approved by the FDA for medical diagnostics (e.g., commercially available from BD Diagnostics, Franklin Lakes, N.J.). These antibodies are selected to specifically recognize the cell receptors that uniquely identify the cell population of interest. Identification and enumeration of the cells in blood that are bound to the monoclonal antibodies is performed using flow cytometry.

Levorotatory β-lactams can also be used in a method for modulating LDL levels, HDL levels, cholesterol levels and the levels of other lipoproteins and apolipoproteins resulting from or derived from LDL, HDL and cholesterol such as apoA, apoB, apoC, and apoE in a subject comprising administering to a subject in need of such treatment a pharmaceutical composition comprising a therapeutically effective amount of a β-lactam; thereby modulating LDL levels, HDL levels and cholesterol levels and the levels of other lipoproteins and apolipoproteins resulting from or derived from LDL, HDL, cholesterol and other lipoproteins and apolipoproteins in the subject.

In one preferred embodiment, the levels of LDL and the levels of other lipoproteins and apolipoproteins resulting from or derived from LDL are lowered.

In another preferred embodiment, the levels of HDL and the levels of other lipoproteins and apolipoproteins resulting from or derived from HDL are increased.

Levorotatory β-lactams can also be used in a method for regulating hematopoiesis to modulate the number of CD4+ T cells and CD8+ T cells in a subject comprising administering to a subject in need of such treatment a pharmaceutical composition comprising a therapeutically effective amount of a β-lactam; thereby modulating the number of CD4+ CD8+ progenitor T cells and the resulting number of CD4+ T cells and CD8+ T cells.

In a still further embodiment, the present invention provides a method for treating patients suffering from congenital α1PI deficiency and suffering from COPD comprising administering to said patients an effective amount of a β-lactam.

In yet another embodiment, the present invention provides a composition of matter comprising the tromethamine salt of L-ampicillin.

In another embodiment, the present invention provides a pharmaceutical composition comprising the tromethamine salt of L-ampicillin and a pharmaceutically acceptable carrier, excipient, or diluent.

The present invention is described below in examples which are intended to further describe the invention without limiting the scope thereof.

Example 1: α1 PI Inhibits SDF-1 Induced Migration of Human Leukemic Cells and Enhances Migration of Human Stem Cells Human acute myeloid leukemia cells (AML) not only secrete HLE-G, but also express HLE-CS constitutively on the cell surface in a manner that is regulated by the CXCR4/SDF-1 axis (Tavor et al., 2005). Pre-incubation of AML cells with α1PI significantly reduced their SDF-1 dependent migration in all AML cells tested using an in vitro transwell assay (Tavor et al., 2005). Further, in a mouse model it was found that α1PI inhibited homing of transplanted human stem cells to bone marrow and egress of transplanted AML cells from bone marrow (Lapidot and Petit, 2002).). The influence was shown to occur by the action of α1PI on HLE-CS (Bristow et al., 2008; Bristow et al., 2012).

When AML cells were treated with α1PI, SDF-1-induced pseudopodia formation was prevented. These results are in contrast to previous studies using a U937 promonocytic cell line which demonstrated that α1PI-induced pseudopodia formation and inhibition of cell migration was prevented by pretreatment with SDF-1 (FIG. 1) (Bristow et al., 2003). This difference was resolved by examining the kinetics of influence of α1PI on cells and emphasizes the importance of α1PI and SDF-1 in promoting cell migration of various cells depending on their stage of differentiation and order of interaction with cells (Bristow et al., 2013).

For the adherence assay, sterile coverslips (12 mm diameter, Sigma) were washed in endotoxin-free water and prepared by delivering a 10 μl volume containing various dilutions of one of the following stimulants in HBSS without calcium and magnesium: CCL3 (MIP-1α, Peprotech, Inc., Rocky Hill, N.J.), α1PI CCL4, (MIP-1β, Peprotech), CCL5, (RANTES, Peprotech), CXCL12, (SDF-1, Peprotech), (Cat. #A6150, lot #82H9323, Sigma), $α_1$PI (A9024, lot #115H9320, Sigma), $α_1$ antichymotrypsin ($α_1$ACT, Calbiochem, La Jolla, Calif.), antithrombin III (ATIII (Sigma), C1 esterase inhibitor (C1inh, Calbiochem), methoxysuccinyl-L-Ala-L-Ala-L-Pro-L-Val-chloromethylketone (MAAPVCK, Sigma), N-tosyl-L-phenylalanine chloromethylketone (TPCK, Sigma), a synthetic peptide representative of the thrombin agonist (SFLLRN, Ser-Phe-Leu-Leu-Arg-Asn), or a synthetic peptide representative of the HIV fusion domain solubilized in 10% EtOH (FLGFL, Phe-Leu-Gly-Phe-Leu).

To coverslips prepared with chemoattractants as described above, $10^6$ cells in 90 μl HBSS were mixed to uniformity, and incubated for 30 min in humidified 5% $CO_2$ at 37° C. without dehydration. To detect interacting effects of stimulants, cells were delivered in an 80 μl volume to coverslips previously prepared with 10 μl of one stimulant, mixed to uniformity, and incubated for 15 min at 37° C. Subsequently, an additional stimulant was delivered in a 10 μl volume to each coverslip, mixed with pre-incubated cells to uniformity, and incubated for 30-60 min at 37° C. After stringently washing coverslips free of non-adherent cells, adherent cells were fixed by incubation for 10 min at 20° C. with 4% paraformaldehyde in PBS containing 2.5 μM of the nuclear staining, acridine orange. Slides were examined by epi-illumination UV microscopy on a Zeiss Axioskop Means and standard deviations were determined by counting adherent cells in at least three fields/coverslip.

Figure 1B:
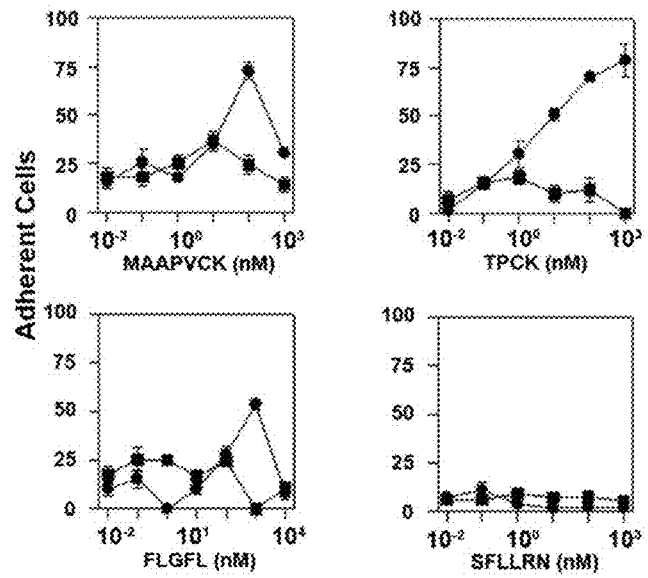
Figure 1C:
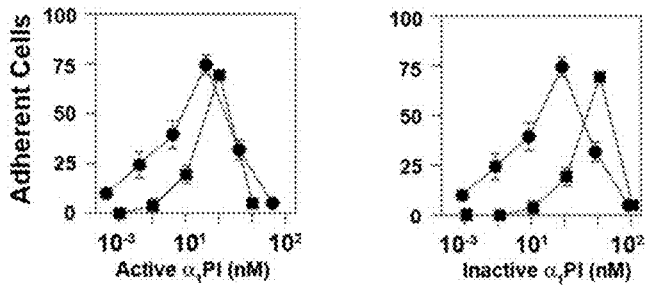

In FIG. 1 is shown that (A) Adherent cells were enumerated in response to chemokines CXCL12α (●), CCL3 (■), CCL4 (▲), and CCL5 (▼) or in response to proteinase inhibitors $α_1$PI (▲), ATIII (■), and $α_1$ACT (●). Means and standard deviations represent the difference between stimulated and unstimulated adherence. (B) Plus clone 10 (●), but not minus clone 17 (■), was stimulated to adhere by MAAPVCK, a synthetic peptide inhibitor for HLE and by TPCK, a synthetic peptide inhibitor for chymotrypsin. Plus clone 10 (●), but not minus clone 17 (■), was stimulated to adhere in response to the HIV fusion peptide (FLGFL). The HIV fusion peptide FLGFL was solubilized in 10% EtOH, and unstimulated adherence of cells incubated with 10% EtOH in the absence of peptide was 36±6 cells/field. Neither subclone was influenced by the thrombin agonist peptide (SFLLRN). Two different preparations of $α_1$PI were determined to be 32.7% (●) and 8.3% active (■). (C) Plus clone 10 stimulated by these two $α_1$PI preparations responded to equivalent optimal concentrations of active $α_1$PI, but different concentrations of inactive $α_1$PI. Adherence was optimized for each chemoattractant and adherence induced by each chemoattractant was enumerated in more than three separate experiments.

Examination of adherence stimulated by various agonists at various time points over a 24-hour period showed that optimal effects could be detected between 30-60 min. Adherence of clones in independent experiments using identical conditions did not vary. Unstimulated adherence of U937 sub clones between independent experiments could be explained in entirety by the bovine serum in which cells had been cultured, suggesting cells were conditioned by unknown serum components as previously demonstrated (Bristow et al., 2001; Bristow et al., 2003).

Example 2: Screening of β-Lactams for Activity; Inhibition of Elastase Proteinase Activity (HLE-G) and Stimulation of Cellular Adherence (HLE-CS)

Compounds were screened for 50% inhibitory activity (IC50) vs 750/1 soluble, granule-associated human leukocyte elastase (HLE-G). As shown in Table 1, α1PI exhibited an IC50 of 380/1, half the concentration of HLE-G consistent with their known equimolar relationship. Cephems, Penams, Monobactams, Penems, and Carbapenems exhibited IC50 average values of 219±48 μM, suggesting that β-lactams are effective for binding to HLE at a molar excess of compound to HLE-G at IC50. As shown in Table 1 below, all 5 classes of β-lactams bind to HLE-G and HLE-CS.

TABLE 1

All 5 classes of β-lactams bind to HLE-G and HLE-CS

| Compound Class | Compound | IC50 (μM)* | Molar Excess** | Adherent Cells | Optimal Adherence Concentration (nM)*** |
|---|---|---|---|---|---|
| Cephems | | | | | |
| | Cephalexin | 134.1 | 1.8 | 27 ± 10 | 10 |
| | Cefuroxine | 166.7 | 2.2 | 34 ± 8 | 1 |
| Penams | | | | | |
| | D-Ampicillin | 280.7 | 3.7 | 47 ± 8 | 1 |
| | Pen V | 262.0 | 3.5 | 30 ± 4 | 10 |
| | Dicloxacillin | 231.6 | 3.1 | 26 ± 9 | 1 |
| | Amoxicillin | 253.1 | 3.4 | 54 ± 20 | 1 |
| | L-Ampicillin | 187.7 | 2.5 | 39 ± 7 | 1 |
| Monobactams | | | | | |
| | Aztreonam | 234.1 | 3.1 | 33 ± 4 | 1 |
| | Ezetimibe | 276.7 | 3.7 | 40 ± 3 | 100 |
| Penems | | | | | |
| | Faropenem | 203.1 | 2.7 | 23 ± 4 | 10 |
| Carbapenems | | | | | |
| | Doripenem | 177.8 | 2.4 | 52 ± 6 | 100 |

*IC50 of compound versus HLE-G (75 μM). For comparison, α1PI is 38 μM at IC50.
**Molar excess of compound to HLE-G at IC50.
***To each compound-treated well was added 2,000 U937 cells. For comparison (see FIG. 1C), the optimal concentration of α1PI is 0.5 nm per 10,000 U937 cells yielding 75 ± 19 adherent cells.

Example 3: L-Ampicillin has Substantially No Antibiotic Activity

To screen for antibiotic activity, the Clinical Laboratory Standards Institute (CLSI) approved protocol for the Kirby-Bauer Disk Test was performed to compare the antibiotic activities of D-ampicillin and L-ampicillin.

D-ampicillin-sensitive *E. coli* DH5-Alpha was cultured overnight in LB broth, and the cell concentration was calibrated using McFarland Turbidity Standard 0.05 for <300×10⁶ CFU. At this concentration of cells, bacteria were spread on Mueller-Hinton agar plates. Filter disks (6 mm diameter) were placed on the agar and to each disk was applied 10 μl of D-ampicillin or L-ampicillin in 10-fold serial dilutions beginning with 50 mM concentration. After incubation for 16 hours at 37° C., plates were examined for zones of inhibition. The results are shown in FIGS. 2A and 2B.

Figures 2A, 2B:
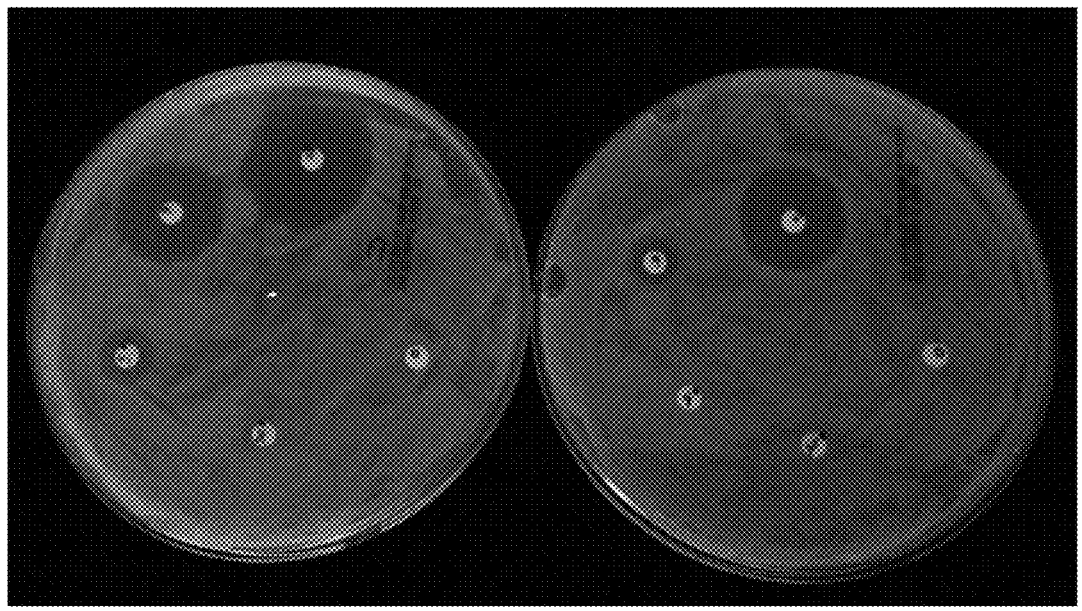
FIGS. 2A and 2B are photographs of Mueller-Hinton agar plates comparing the antibiotic activity of D-ampicillin (2A) with the antibiotic activity of L-ampicillin (2B).

In FIG. 2A the diameters of the zones of inhibition of 5 mM and 0.5 mM D-ampicillin (3 cm at 10 o'clock and 1.5 cm at 8 o'clock, respectively) were equivalent to the diameters of the zones of inhibition of 50 mM and 5 mM L-isomer (2.8 cm at 12 o'clock and 1.4 cm at 10 o'clock, respectively) in FIG. 2B. These results demonstrate that the L-isomer has 10-fold less antibiotic activity compared to D-ampicillin.

The pediatric dose of D-ampicillin is 50-100 mg/kg/day (every 6 hr.), and pediatric blood volume is 70 ml/kg, thus the pediatric dose of D-ampicillin is 50-100 mg/70 ml which is equivalent to 2-4 mM/day or 0.7-1.3 mM every 6 hr (q6 hr). The commonly used adult dose is 750-1500 mg/day (q6 hr), and adult blood volume is 5 L which is equivalent to 0.4-0.9 mM/day or 0.2-0.3 mM q6 hr. D-ampicillin exhibits activity in the Kirby-Bauer Disk Test at 0.5 mM which is within the range of the pediatric dose and exceeds the adult dose. However, L-ampicillin shows equivalent activity at 10-fold higher concentration (5 mM) and is ineffective as an antibiotic at 0.5 mM concentration demonstrating that it is ineffective as an antibiotic if used at this dosage. The 2014 Clinical & Laboratory Standards Institute (CLSI) criteria for ampicillin-resistant vs susceptible *E. coli* is a 4-fold dosage difference. Because the dosage difference between D-ampicillin and L-ampicillin is 10-fold, L-ampicillin is not an effective antibiotic (Table 2A, 2014 CLSI M100-S24) (CLSI, 2014).

Example 4: Stimulation of Cell Migration and Endocytosis by L-Ampicillin

Receptor Polarization: U937 Clone 10 cells were cultured overnight in AIM-V serum-free medium. Cells were pelleted, re-suspended in AIM-V at 2×10⁶/ml, and 250 μl (5×10⁵ cells) was added to Eppendorf tubes pre-coated to prevent attachment. Cells were preconditioned with a positive control (α1PI, either PROLASTIN®-C or ZEMIRA®), D-ampicillin, L-ampicillin, or negative control (AIM-V medium) for 15 min at 37° C., 5% $CO_2$ to induce polarization of functionally-related plasma-membrane receptors including cell surface human leukocyte elastase (HLE-CS), CD4+, CXCR4, T cell antigen receptor (TcR), and the very low density lipoprotein receptor (VLDLR) as previously shown (Bristow, et al., 2013).

Binding and Endocytosis: AT 2 chemically inactivated SHIV preparations, consisting of non-infectious virus with conformationally and functionally intact envelope glycoproteins, were provided by the AIDS Vaccine Program (SAIC Frederick, Frederick, Md.). Cells were pulsed with virus (30 ng p27 or p24 per 10⁶ cells) for 2 hr. at 2° C. which allows binding, but prevents endocytosis. Alternatively, cells were pulsed with virus for 2 hr. at 37° C. which allows binding and endocytosis. Following pulsing for 2 hr., cells were mounted on Alcian blue slides for microscopy. The presence of inactivated virus in test cells was detected using dodecameric human CD4+-IgG1 provided by the Laboratory of Immunoregulation, NIAID, NIH. This reagent specifically recognizes conformationally intact HIV 1/SIV envelope gp120. CD4-IgG1 was detected using HRP-conjugated Rb anti-human IgG (Sigma). CD4+ IgG-labeled cells were coupled to Oregon 488 fluorochrome using the tyramide signal amplification system (Life Science Products, Boston, Mass., USA). In some cases, cells stained on slides were permeabilized using 0.05% saponin during the blocking step and further stained with the nuclear staining dye, 4',6-diamidino-2-phenylindole (DAPI), mounted, and examined using epifluorescence microscopy using a Zeiss Axioplan or by confocal microscopy using a Perkin Elmer Operetta High Content Imaging System. Cells were analyzed using 2 μm scanning from 3B.

Confocal images of cells preconditioned with L-ampicillin were captured 6 μm above the attached surface of the cells.

Figures 3A, 3B:
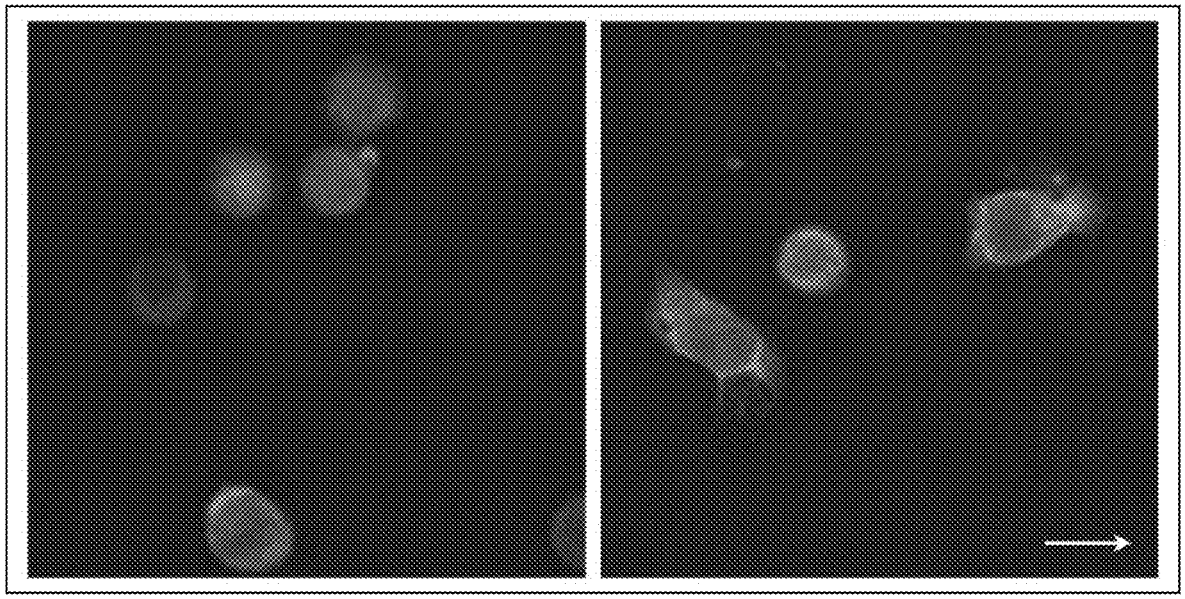
FIGS. 3A and 3B are photographs showing the stimulation of cell migration and endocytosis induced by L-ampicillin.

The results are shown in FIGS. 3A and 3B. In FIG. 3A, cells maintained at 2° C. exhibited receptor polarization. SHIV was detected only on the plasma membrane of polarized cells, never internal to the cells. Cells were rounded and exhibited no evidence of cell migration. In FIG. 3B, cells maintained at 37° C. exhibited an extending leading edge and retracting trailing edge characteristic of cell migration. SHIV was detected internal to the cells, prominently along tubular structures at the leading edges and in endosomes at the trailing edges of migrating cells. There was no SHIV binding in the presence of buffer alone (not depicted). DAPI represents nuclei. Bar represents 25 µm, and arrow depicts direction of locomotion of migrating cells.

Example 5: L-Ampicillin Lowers LDL Levels

Figure 4:
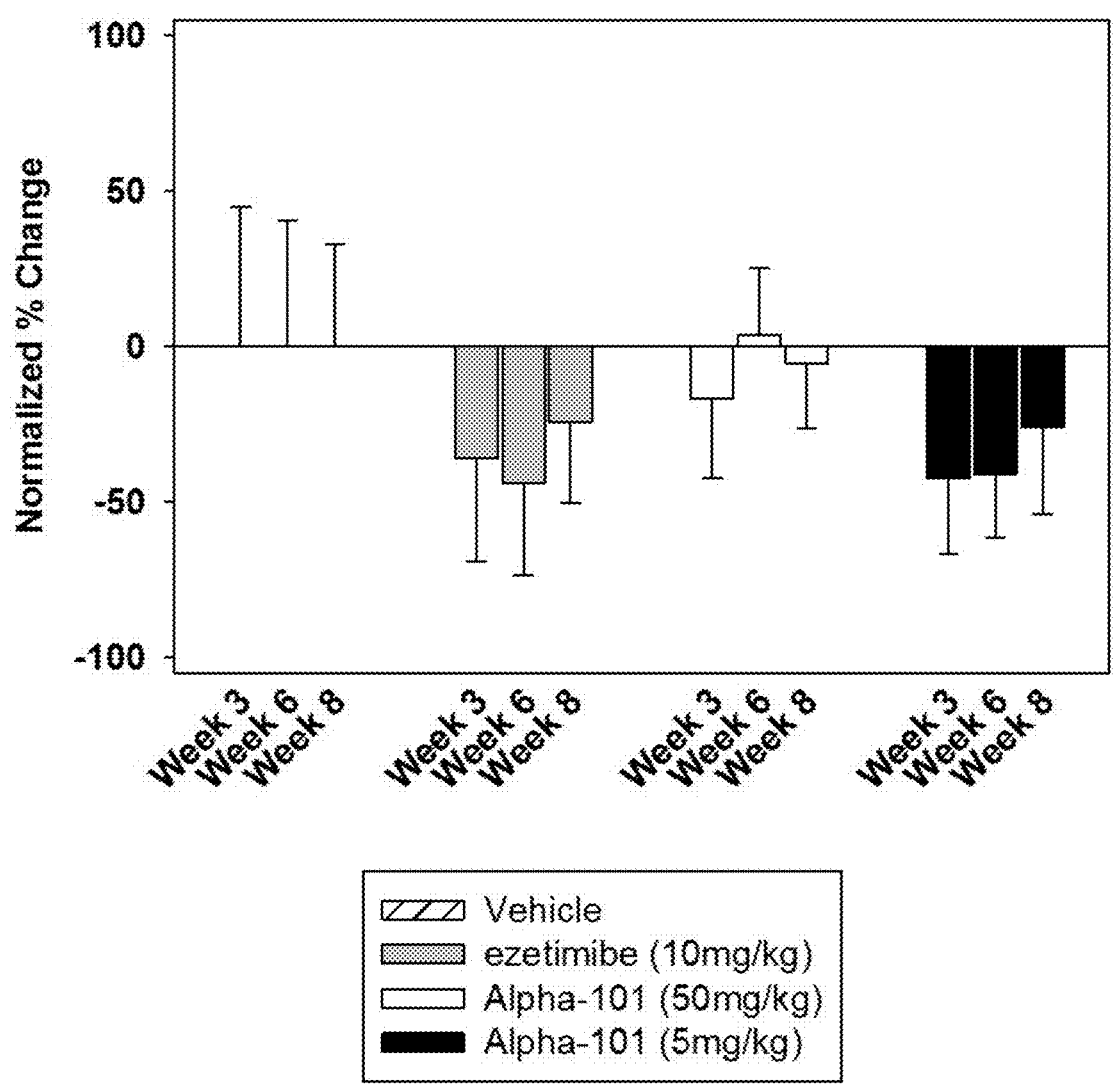
FIG. 4 is a graph showing the normalized % change in LDL levels in Diet-induced obesity mice (DIO) mice treated pursuant to the present invention with vehicle, ezetimibe (10 mg/kg), L-ampicillin (50 mg/kg), or L-ampicillin (5 mg/kg).

The well-known Jackson Laboratory (Bar Harbor, Me.) C57BL/6 Diet-Induced Obesity (DIO) mouse model represents human metabolic syndrome and elevated LDL levels. Mice are fed a high fat diet (60% fat) or normal diet (10% fat) for various periods of time and lipoprotein levels were measured. As compared to the 10% DIO, the 60% DIO have significantly elevated total cholesterol, HDL and LDL levels ($p<0.001$), but not triglyceride levels (Tg) (FIG. 4).

Mice received daily treatment with ezetimibe (10 mg/kg) or L-ampicillin (50 mg/kg or 5 mg/kg) by oral gavage.

In accordance with a protocol used in a recently conducted human clinical trial (NCT01731691), mouse peripheral blood was collected into blood collection tubes, and serum was analyzed for lipoprotein levels using Beckman Coulter AU680 Chemistry System. In addition, cells were analyzed by flow cytometry to quantitate lymphocyte subsets including CD3, CD4, and CD8. As compared to baseline levels (before treatment), lipoprotein levels (including, but not limited to total cholesterol, HDL, LDL, apoA, apoB, apoC, apoE) and blood cells expressing the above mentioned cellular markers were quantitated to determine changes due to treatment.

Diet-induced obesity mice (DIO, Jackson Laboratory) were fed a 60% fat diet for 17 weeks. Twelve mice were assigned to each of 4 arms of the study including a vehicle control (Group 1), ezetimibe (Zetia, Cayman Chemical), 10 mg/kg, (Group 2), L-ampicillin (50 mg/kg), (Group 3), and L-ampicillin (5 mg/kg, (Group 4). The compounds were delivered by oral gavage 5 days per week. Serum samples were collected on weeks 3, 6 and 8 and were analyzed for levels of glucose, total cholesterol, triglycerides, HDL, LDL, and non-esterified fatty acids.

Because mice were maintained on the DIO diet throughout the study, body weight and LDL levels increased in the vehicle control (Group 1). To compare the effectiveness of compounds, mean values within each treatment group were normalized by forming a ratio to mean values of vehicle, and the ratio was expressed as normalized % change using to the formula:

$$100-(\text{Treatment mean/Vehicle mean}*100).$$

The results are shown in FIG. 4. At week 6, the normalized mean % change for L-ampicillin, 5 mg/kg (Group 4, black bars) was $-41.0\pm20.5\%$ and for ezetimibe (Group 2, grey bars) was $-43.8\pm29.6\%$, significantly lower ($P=0.001$) than vehicle (Group 1, hatched bars) or L-ampicillin, 50 mg/kg (Group 3, white bars) (10% and 3.7%, respectively).

Example 6: Chemical Synthesis of L-Ampicillin

The step by step chemical synthesis of the compound is described in detail.

Figure 9:
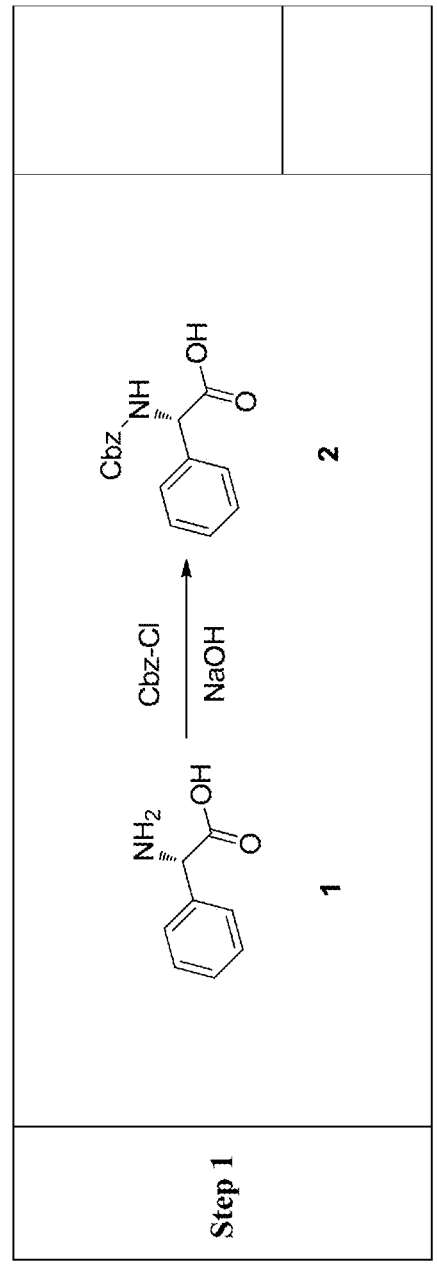
FIG. 9 is a table showing the reaction of phenylamine carboxylic acid with benzyl carbonochloridate in synthesis of the tromethamine salt of L-ampicillin.
Figure 10:
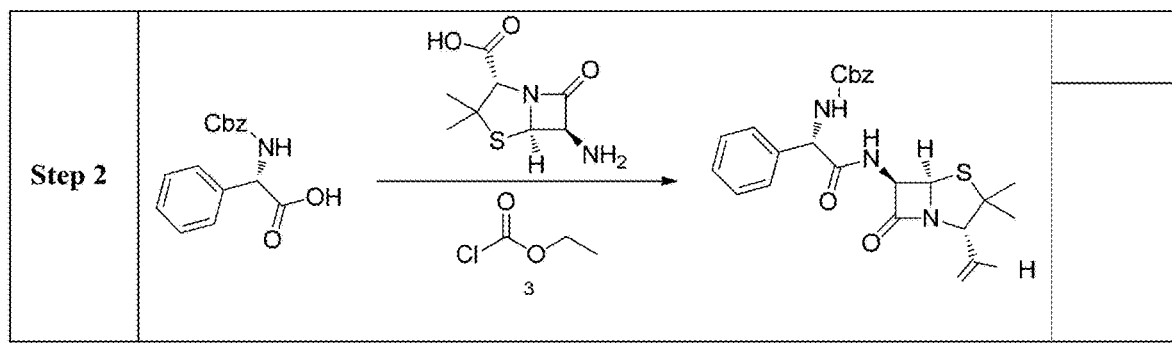
FIG. 10 is a table showing the reaction of ethyl chloroformate and triethylamine with 6-aminopenicillinic acid in the synthesis of the tromethamine salt of L-amplicillin.
Figure 11:
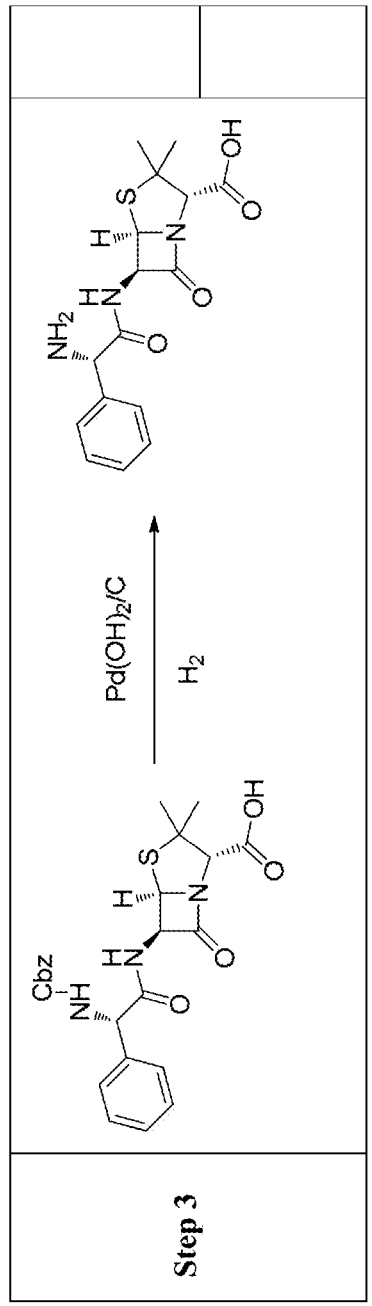
FIG. 11 is a table showing the reaction with compound 3 and THF in the synthesis of the tromethamine salt of L-ampicillin.

See FIG. 9 (Step 1) for a Reaction of phenylamine carboxylic acid with benzyl carbonochloridate in synthesis of the tromethamine salt of L-ampicillin.
Procedure:
Compound 1 (phenylamine carboxylic acid is synthesized from toluene. To a solution of compound 1 (500 mg, 3.31 mmol) (Wuxi Biortus Biosciences, Jiangyin, Jiangsu, P.R. China) in 2N sodium hydroxide (1.65 ml, 3.31 mmol) stirred at 0° C., benzyl carbonochloridate (512 µL, 3.64 mmol) and 2N sodium hydroxide (1.82 ml, 3.64 mmol) were simultaneously added dropwise from two different syringes.
The reaction was stirred at RT for 45 minutes and a precipitate appeared.
Water was added and the solution was extracted with $Et_2O$. The aqueous phase was acidified with 1N HCl and the desired product was extracted again with $Et_2O$. The combined organic phases were dried over $Na_2SO_4$, filtered and evaporated to obtain title product (855 mg, 91% yield) as a white solid.
See FIG. 10 (Step 2) for a Reaction of ethyl chloroformate and triethylamine with 6- aminopenicillinic acid in the synthesis of the tromethamine salt of L-amplicilln.
Procedure:
Ethyl chloroformate (247 mg, 2.3 mmol) was added to an ice cold solution of compound 2 (500 mg, 1.75 mmol), and triethylamine (231 mg, 2.3 mmoles) in dry acetone (20 mL).
The mixture was stirred at 0° C for 10 minutes.
Then the suspension was cooled to −50° C. and stirred vigorously during addition as rapidly as possible of an ice-cold solution of 6-aminopenicillinic acid (417 mg, 1.93 mmol) in 3 percent sodium bicarbonate.
The reaction mixture was stirred at 0° C. for one hour. The reaction mixture was allowed to reach room temperature over a period of 30 minutes. Then the reaction mixture was concentrated under vacuum and then washed with ether (3 × 100 mL). The aqueous layer was acidified to pH 2 using ice cold dilute HCl and quickly extracted with ether. The reaction mixture was concentrated under vacuum. The residue was purified by silica gel column chromatography with Hex/EtOAc (1/1) to provide the title product (400 mg, 35% yield) as a white solid.
See FIG. 11 (Step 3) for a Reaction with compound 3 and THF in the synthesis of the tromethamine salt of L-ampicillin.
Procedure:
To a solution of compound 3 (1.4 g, 2.9 mmol) in 100 mL of THF and 80 mL of water was added 1.4 g. of 20 percent $Pd(OH)_2/C$
The mixture was shaken under an atmosphere of hydrogen at a pressure of 50 psi for 1.5 hours.
At this point the catalyst was removed by filtration and 1 g of fresh catalyst was added.
The mixture was shaken under hydrogen at 50 psi for a further 1 hour.
The catalyst was removed by filtration with celite and the bulk of the THF was removed by evaporation in vacuo.
The pH of the residual aqueous phase was adjusted to 5.0 using AcOH and the acidified solution was extracted with ethyl acetate (3 × 50 mL).
The aqueous phase was lyophilized.
250 mg (24.71% yield) of the white solid was obtained.

-continued

Figure 12:
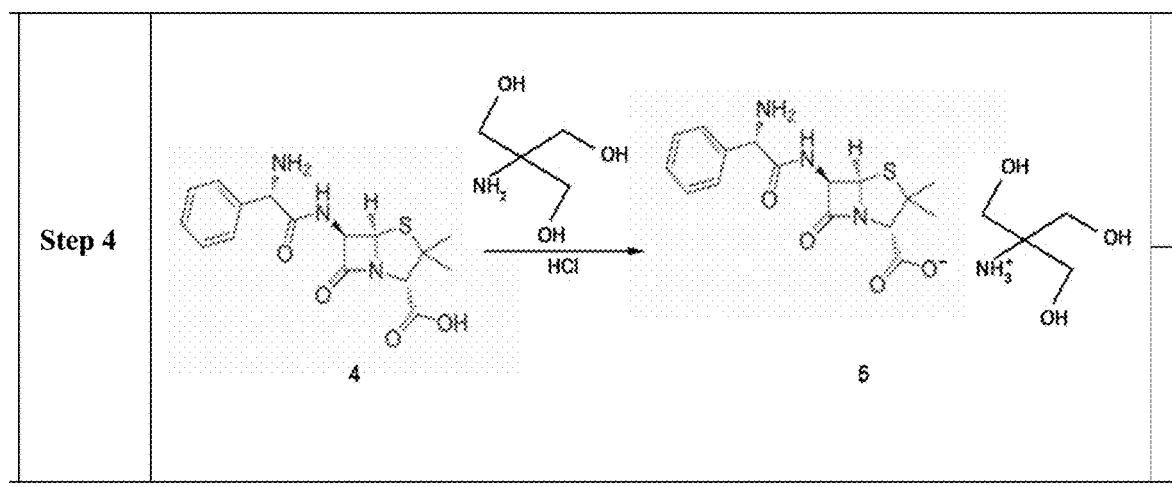
FIG. 12 is a table showing the reaction of compound 4 with 1M C4H11NO3 in the synthesis of the tromethamine salt of L-ampicillin.

See FIG. 12 (Step 4) for a Reaction of compound 4 with 1M C4H11NO3 in the synthesis of the tromethamine salt of L-ampicillin.
Procedure:
To compound 4 was added 1M $C_4H_{11}NO_3$ + 0.22M HCl (1 g/30 mL) followed by 1.8 L saline producing an orally available solution (53 mM). Compound 5 is the tromethamine salt of L-ampicillin.

Example 7: α1PI in Hematopoiesis in Normal, Healthy Individuals

It has been previously demonstrated that in HIV-1 uninfected individuals CD4+ T lymphocyte counts (hereinafter "CD4 counts) are regulated by the number of cells expressing cell surface human leukocyte elastase (HLE-CS, active α1PI levels, and the number of cells expressing the chemokine receptor CXCR4 ($r2=0.92$, p, 0.001, n=31; Table 1 of referenced publication (Bristow et al., 2012). In HIV-1 infected patients, active α1PI becomes deficient due to disease processes, a situation in which active α1PI becomes rate limiting for CD4+ counts (Table 1 of referenced publication (Bristow et al., 2001). The present inventors demonstrated that active α1PI is strongly correlated with CD4+ counts in HIV-1 infected individuals ($r2=0.927$, $p<0.0001$, $n=26$; FIG. 1 of referenced publication (4).

In a clinical trial, it was demonstrated that therapeutic α1PI administration caused an increase in CD4+ counts in HIV-1-infected patients with acquired α1PI deficiency due to HIV-1 infection and in HIV-1 uninfected patients with inherited α1PI deficiency. This confirms that α1PI regulates CD4+ counts in the presence or absence of HIV-1 disease (FIG. 1 of referenced publication (Bristow et al., 2010)). It was demonstrated that the mechanism by which α1PI regulates CD4+ counts is by inducing the migration of cells through tissue, specifically through the thymus where CD4+ T-lymphocytes are generated. The binding of circulating α1PI to T-lymphocytes that express HLE-CS (the receptor that binds to active α1PI) and receptors for very low density lipoprotein (VLDLR, the receptor that binds to inactive α1PI) results in conformational changes that promote the binding of the α1PI-HLE-CS complex to VLDLR on the same cells, a situation that induces endocytosis of the receptor aggregate and forward movement of the cell (Bristow et al., 2013).

New evidence (unpublished observations) demonstrates that in HIV-1 uninfected individuals, CD4+ counts are linearly correlated with the combination of 4 variables, 1) the number of T-lymphocytes (Ly) expressing HLE-CS and VLDLR, 2) active α1PI levels, 3) inactive α1PI levels, and 4) T cell antigen receptor rearrangement excision circles (sjβTRECs, a biomarker specific for the generation of new T-lymphocytes). This evidence confirms that α1PI induces generation of new CD4+ cells from progenitor cells (Table 2). The mechanism by which α1PI regulates CD4+ counts is by inducing the migration of hematopoietic progenitor cells through the thymus (thymopoiesis). As expected, B cells (CD19+) were not found to be correlated with sjβTRECs ($r=-0.221$, $P=0.259$, $n=28$), but were linearly correlated with HLE-CS+ VLDLR+ T-lymphocytes, active and inactive α1PI levels (Table 2). Surprisingly, red blood cells (RBC) were also linearly correlated with HLE-CS+ VLDLR+ T-lymphocytes, active and inactive α1PI levels (Table 2). Neutrophils and monocytic cells were not correlated with any of these variables (Table 2). The mechanism by which α1PI regulates CD4+ counts is by inducing the migration of hematopoietic progenitor cells through the thymus (thymopoiesis). As expected, B cells (CD19+) were not found to be correlated with sjβTRECs ($r=-0.221$, $P=0.259$, $n=28$), but were linearly correlated with HLE-CS+ VLDLR+ T-lymphocytes, active and inactive α1PI levels (Table 2). Surprisingly, red blood cells (RBC) were also linearly correlated with HLE-CS+ VLDLR+ T-lymphocytes, active and inactive α1PI levels (Table 2). Neutrophils and monocytic cells were not correlated with any of these variables (Table 2).

Thymopoiesis occurs before birth and continues through adulthood into the geriatric stage of life when the thymus loses the capacity to produce new CD4+ T-lymphocytes. Thus, therapeutic α1PI, and pursuant to the present invention, β-lactams are indicated in the treatment or prophylaxis of secondary immune deficiency when the number of CD4+ T-lymphocytes is below normal or predicted to become below normal. Secondary immune deficiencies, also known as acquired immunodeficiencies, can result from various immunosuppressive agents. For example, malnutrition, aging and particular medications (e.g. chemotherapy, disease-modifying immunosuppressive drugs administered after organ transplants, glucocorticoids). In addition, α1PI, and pursuant to the present invention, β-lactams are similarly indicated in the treatment of individuals with metabolic syndrome who have elevated LDL levels.

From the human clinical trial, the following correlations were found:

1) Increased total cholesterol and LDL were correlated with increased apoB100 ($r=0.82$, $P=2E-07$, $n=36$ and $r=0.89$, $P=2E-07$, $n=36$, respectively). This is expected because it is well known that apoB100 binds to LDL (Veniant et al., 1998);

2) Increased triglycerides were correlated with increased apoB48 ($r=0.89$, $P=2E-07$, $n=36$) and increased CD4+ T-lymphocytes, and the correlation was amplified by α1PI therapy in HIV-1 disease ($r=0.48$, $P=0.014$, $n=26$), but with decreased monocytes ($r=-0.69$, $P<2E-07$, $n=36$). This is expected because it is well known that apoB48 binds to triglycerides and that triglycerides are primarily transported by CD4+ T cells (Stalenhoef et al., 1984; Bristow et al., 2013);

3) Increased HDL was correlated with increased apoA1 ($r=0.82$, $P<9.7E-10$, $n=36$); This is expected because it is well known that apoA1 binds to HDL (Fagerberg et al., 2014).

4) Increased total α1PI was correlated with decreased CD3+ T-lymphocytes ($r=-0.66$, $P<1E-06$, $n=36$ and decreased CD8+ T-lymphocytes in which case the correlation was amplified by α1PI therapy ($r=-0.69$, $P<8E-05$, $n=25$). This is expected because it was found that increased α1PI is correlated with increased CD4+ T lymphocytes and increased CD4+ T lymphocytes are correlated with decreased CD8+ T lymphocytes (Bristow et al., 2012).

Unexpected results demonstrated the regulation of lipoproteins by α1PI therapy:

1) Increased total α1PI was correlated with decreased apoB48, and the correlation was amplified by α1PI therapy in HIV-1 disease (r=−0.80, P<2E-06, n=26);
2) Increased active α1PI was correlated with decreased HDL (r=−0.51, P<0.002, n=36);
3) Increased HDL was correlated with increased apoA1 (r=0.82, P<9.7E-10, n=36); This is expected because it is well known that apoA1 binds to HDL (Fagerberg et al., 2014).
4) Increased active α1PI was correlated with decreased apoA1 (r=−0.61, P=7E-05, n=36);
5) Increased active α1PI was correlated with decreased lymphocytes (r=−0.66, P=7.7E-06, n=36);
6) Increased inactive α1PI was correlated with increased lymphocytes, and the correlation was amplified by α1PI therapy in HIV-1 disease (r=0.42, P=0.037, n=26);
7) Increased apoB100 was correlated with increased platelets, and the correlation was amplified by α1PI therapy in HIV-1 disease (r=0.46, P=0.018, n=26);
8) Increased apoB48 was correlated with decreased CD19% (% B cells) and decreased red blood cells (r=−0.38, P=0.24, n=36 and r=−0.33, P=0.05, n=36, respectively);
9) Increased apoB48 was correlated with decreased total α1PI, and the correlation was amplified by α1PI therapy in HIV-1 disease (r=−0.80, P=2E-07, n=26);
10) Increased total α1PI was correlated with increased apoB100 (r=0.66, P=9E-06, n=36);
11) Increased total α1PI was correlated with decreased apoE (r=−0.56, P=5E-04, n=35);
12) Increased total α1PI was correlated with decreased % CD3+HLE+ T lymphocytes (r=−0.41, P=0.014, n=35) and decreased CD3+HLE+ T lymphocytes (r=−0.14, P=0.014, n=35), but not after treatment;
13) Increased total α1PI was correlated with increased sjβTRECs, a marker of newly generated CD4 T cells (r=0.42, P=0.057, n=21).

These results are unexpected because the relationships between α1PI and lipoproteins other than LDL have not previously been reported. These unexpected results demonstrate that triglycerides, using apoB48, are transported via CD4+ cells from the gut through lymph to blood and further, that increased total α1PI decreases CD4+ cells and decreases apoB48. Interestingly, α1PI therapy in HIV-1 disease amplified the correlation between increased total α1PI and decreased apoB48 demonstrating that α1PI regulates apoB48 levels and that α1PI and apoB48 levels are in feedback regulation in the same manner that α1PI is in feedback regulation with LDL levels (Bristow et al., 2013). These data demonstrate that increased α1PI produces decreased apoB48 thereby decreasing the capacity to absorb dietary fats which results in decreased triglyceride levels. Because LDL levels can be calculated using the Friedwald formula as LDL (mg/dL)=total cholesterol (mg/dL)−HDL (mg/dL)−triglycerides (mg/dL)/5, these results show that lowering triglycerides directly lowers LDL levels. Increased total α1PI was correlated with decreased CD3+HLE+ T-lymphocytes (early T cells) and with increased sjβTRECs (early thymic emigrants) supporting previously reports that the generation and fate of T cells are regulated by α1PI.

TABLE 2

Multiple Linear Regression Analysis of Blood Cell Counts in Normal, Healthy Individuals.

| | Independent Variables | | | |
|---|---|---|---|---|
| | $HLE_{CS}^+$ $VLDLR^+$ Ly 262 ± 322 events, n = 35[a] | Active α1PI 22 ± 12μM, n = 36 | Inactive α1PI 17 ± 11 μM, n = 36 | sjβTRECs 403 ± 355 pM, n = 28 |
| Dependent Variables | | | | | Multilinear Regression[b] |
| CD4 ± Ly 758 ± 273 cells/μl, n = 36 | P = 0.007 | P < 0.001 | P = 0.006 | P = 0.034 | $r^2$ = 0.65, P < 0.001, n = 27 |
| CD19+ Ly 201 ± 62 cells/μl, n = 36 | P = 0.012 | P < 0.001 | P < 0.001 | NA | $r^2$ = 0.45, P < 0.001, n = 35 |
| RBC 5000 ± 500*10^6 cells/μl, n = 36 | P = 0.012 | P = 0.026 | P < 0.001 | NA | $r^2$ = 0.79, P < 0.001, n = 35 |
| Neutrophils 3.2 ± 1.3*10^6 cells/μl, n = 36 | P = 0.113 | P = 0.118 | P = 0243 | NA | $r^2$ = 0.10, P = 0.352, n = 35 |
| Monocytic cells 0.3 ± 0.7*10^6 cells/μl, n = 36 | P = 0.132 | P = 0.200 | P = 0.302 | NA | $r^2$ = 0.08, P = 0.464, n = 35 |

[a]Measurements were obtained from 9 weekly blood samples obtained from 4 normal, healthy individuals. Values for independent and dependent variables represent mean ± standard deviation. Cell counts represent absolute values. $HLE_{CS}^+VLDLR^+$ cells were quantitated in the $CD3^+CD4^+$ lymphocyte gate (Ly) using flow cytometry. Active and inactive α1PI levels were quantitated in serum as previously described (Bristow et al., 1998).
[b]Multilinear regression was performed to determine the relationship of the dependent variables to the independent variables using power of test α = 0.05. Dependent variables were considered to be significantly related to the independent variable if they contributed significantly to the multilinear regression (P < 0.05).

Example 8: cDNA Microarray Analysis Demonstrating Feedback Regulation Between Elastase Inhibitors and Lipoproteins To examine whether α1PI regulates lipoprotein levels by participating in a regulatory pathway at the cellular level, cDNA microarray analysis was performed on two independent primary culture preparations and DNA microarray runs. Probe sets ending with x at and s, at were deleted from analysis, Monocytic cells (Mo/MO) harvested from 1 uninfected individual and 2 HIV-1 infected individuals on ritonavir therapy were analyzed to determine the differential expression patterns of 18,400 genes including 14,500 functionally characterized genes and 3,900 expressed sequence tag clusters, as previously reported (Modarresi et al., 2009). The data were obtained using large-scale microarrays performed on two independent primary culture preparations and DNA microarray runs and the gene expression ratio of HIV-1 infected to uninfected cells was calculated (Modarresi et al., 2009). All of the genes with lipoprotein and proteinase inhibitor functions that changed more than 2-fold are depicted. Probe sets ending with x at and s, at were deleted from analysis. The results are shown in FIG. 5.

Figure 5:
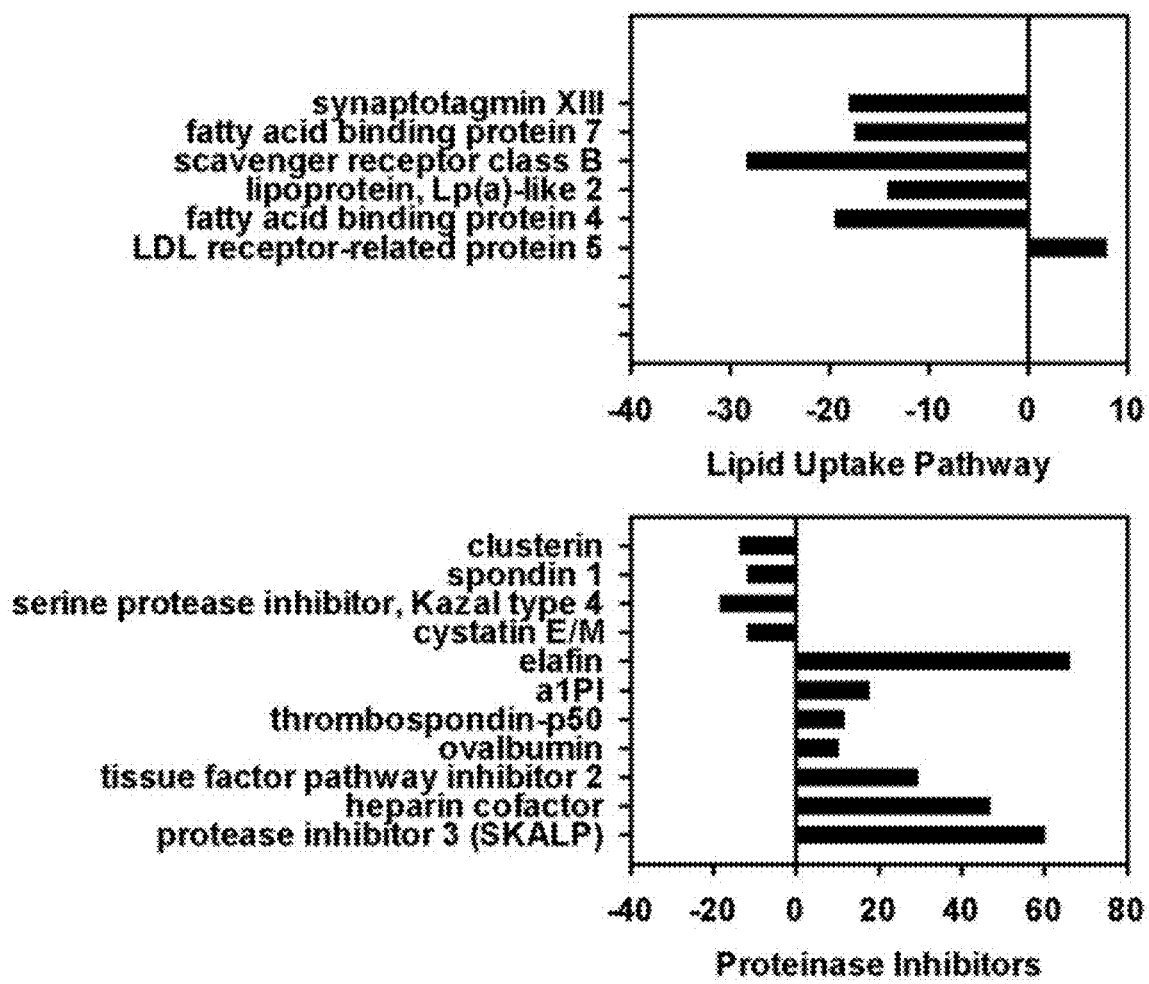
FIG. 5 is a cDNA microarray analysis performed using peripheral mononuclear blood cells (PMBC) harvested from 1 uninfected, untreated volunteer and 2 HIV-1 infected individuals on ritonavir therapy; the gene expression ratio of HIV-1 infected to uninfected cells was calculated

Analysis of gene expression showed that 7 proteinase inhibitors were upregulated in cells from HIV-1 infected individuals compared to cells from an HIV-1 uninfected control (FIG. 5). Of these, 5 are known to bind to human leukocyte elastase (HLE) including ovalbumin (>254 fold), elafin (>66 fold), skin-derived anti-leukoproteinase (>60 fold), thrombospondin (>50 fold), and α1PI (>17 fold); 1 binds α1PI (heparin cofactor, >46 fold); and 1 binds LDL (Tissue Factor Pathway Inhibitor, >99 fold). The levels of 4 other proteinase inhibitors were decreased >12 fold, but none of these inhibitors are known to bind HLE, α1PI, or lipoproteins. LDL receptor (LDLR) and LDL receptor-related protein 5 (LRP5) were increased 4-fold and 8-fold, respectively (data not shown).

By contrast, the expression of 10 of 12 LDL-binding lipoproteins was decreased >2 fold, including scavenger receptor class B (>28 fold), fatty acid binding protein 4 (>19 fold), synaptotagmin III (>18 fold), fatty acid binding protein 7 (>17 fold), lipoprotein Lp(a)-like 2 (>14 fold), apolipoprotein L5 (>5 fold), apolipoprotein E (>4 fold), apolipoprotein B mRNA editing protein (>3 fold), and apolipoprotein C-IV (>2 fold) and apolipoprotein L6 (>2 fold). Two lipoproteins were upregulated, apolipoprotein D (>6 fold) and LDL receptor-related protein 5 (>8 fold).

Because α1PI treatment produced decreased LDL in subjects, this microarray analysis demonstrates that α1PI is in negative feedback regulation with LDL and many other lipoproteins.

Example 9: β-Lactam Compounds for Use in the Present Invention

Presented below are compounds which were screened for use in the present invention. Two different assays were used as set forth below. In order to be used in the present invention the compounds must have at least the same activity as D-ampicillin in both assays.

Assay 1: Inhibition of HLE (microplate assay, 10 tests per plate) as described in Example 2 above and previously published (Bristow et al., 1998). This assay demonstrates the effective binding of the compound to soluble human leukocyte elastase (HLE-G). D-ampicillin was included as a comparison of potency. Each compound was tested in 2-fold serial dilutions with final concentrations of 0.016 µM to 204 versus a constant concentration of 0.5 µM elastase.

Assay 2: Adherence of cells to compound-coated glass (microwell microscope slides, 5 tests per slide) as previously published (Bristow et al., 2008). Adherence is the first step in cell migration and requires no calcium, magnesium, signaling, or energy. This assay demonstrates the effective binding of the compound to cell surface human leukocyte elastase (HLE-CS). As described in Example 1 above, to each well of a 10-well microscope slide is added 10 µl of compound at 10-fold serial dilutions with final concentrations of 0.1 nM to 100 nM per well. To each well was added $1 \times 10^4$ cells. After washing and fixing the cells, the number of adherent cells were counted microscopically.

Compounds Tested (n=11):
  I. Cephalosporins (Cephems)
    1) Cephalexin (CAS #15686-71-2) (Cayman Chemical 9002009)
    2) Cefuroxime (CAS #55268-75-2) (American Custom Chemicals Corp. API0001919)
  II. Penicillins (Penams)
    1) Ampicillin (reference activity) (CAS #63-53-4) (American Custom Chemicals Corp. API0001474)
    2) Penicillin V (CAS #87-08-1) (American Custom Chemicals Corp. API0000755)
    3) Dicloxacillin (CAS #3116-76-5) (American Custom Chemicals Corp. API0004676)
    4) Amoxicillin (CAS #34642-77-8) (American Custom Chemicals Corp. API0015005)
    5) L-Ampicillin (CAS #19379-33-0)
  III. Monobactams
    1) Aztreonam (CAS #78110-38-0) (American Custom Chemicals Corp. API0001576)
    2) Ezetimibe (CAS #163222-33-1) (American Custom Chemicals Corp. API0002672)
  IV. Penems
    1) Faropenem (CAS #122547-49-3) (American Custom Chemicals Corp. API0002676)
  V. Carbapenems
    1) Doripenem (CAS #148016-81-3) (American Custom Chemicals Corp. API0000543)

Example 10: In Vivo Pre-Clinical Study: Effects of L-Ampicillin on T Cell Numbers To examine the ability of L-ampicillin to elevate T lymphocytes, C57BL6 mice (6 mice/arm, 2 arms) were administered vehicle control (group 1) or L-ampicillin (5 mg/kg, Group 2). Compounds were delivered by oral gavage 5 days per week. Blood was collected weekly for detection of CD3e, CD4, and CD8a T cells by flow cytometry using the mouse T lymphocyte subset antibody cocktail with isotype control (BD Biosciences). The study was performed at the Division of Laboratory Animal Research, Stony Brook University, Stony Brook, N.Y. Staining and statistical analysis was performed by Alpha-1 Biologics, and the samples were acquired by the Flow Cytometry Laboratory, Stony Brook Hospital, using a BD LSRFortessa instrument.

Figure 6A:
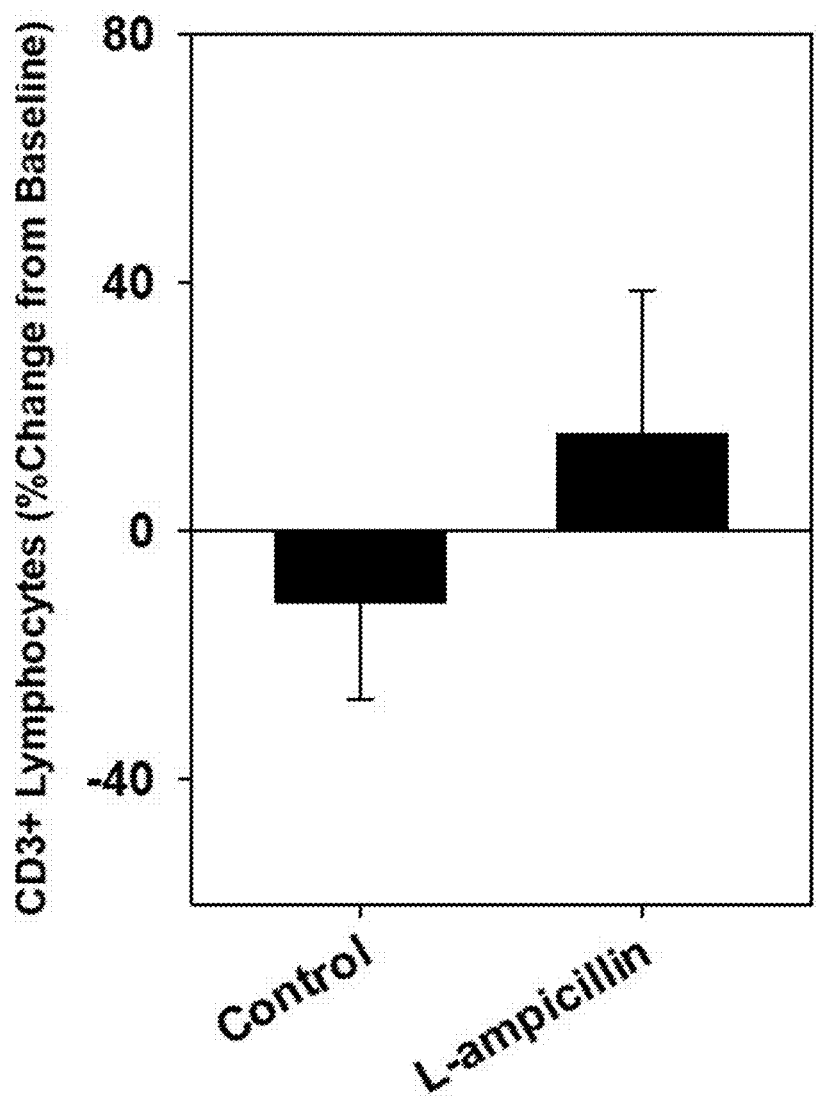
FIGS. 6A and 6B are graphs showing the changes in the number of T lymphocytes (FIG. 6A) and T progenitor cells (FIG. 6B) following 2 weeks of treatment with L-ampicillin.
Figure 6B:
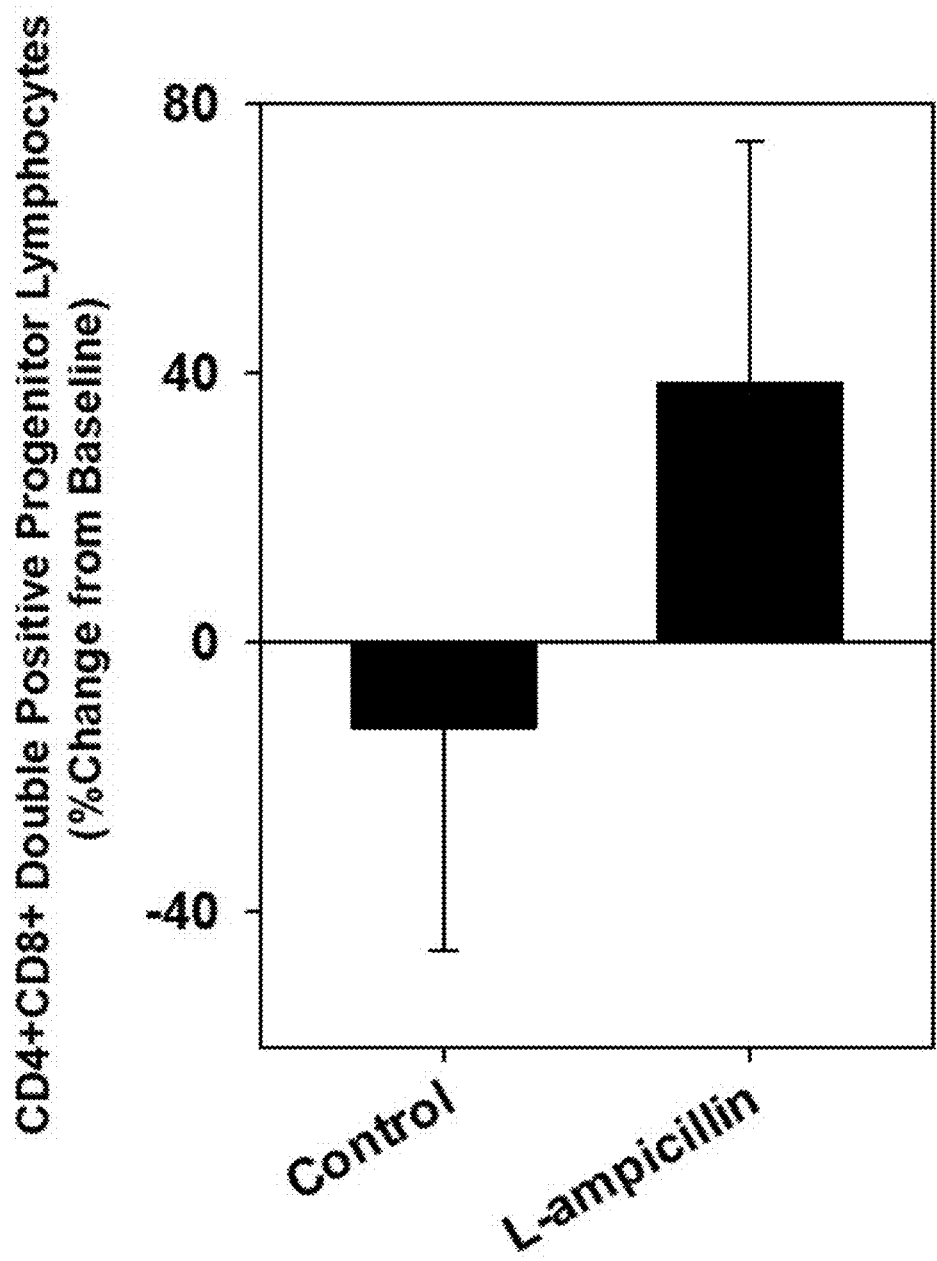

Following 2 weeks of treatment with L-ampicillin, as compared with vehicle control, there was a statistically significant increase in CD3+ T cells ($P<0.05$) (FIG. 6A) and CD4+CD8+ double positive immature, progenitor T cells ($P<0.04$) (FIG. 6B). Data were normally distributed and compared using Student's T-test. Mean % Change in CD3+ T cells for vehicle was −11% and for CD4+CD8+ progenitors was −13%. Mean % Change in CD3+ T cells for L-ampicillin (5 mg/kg) was +16% and for CD4+CD8+ progenitors was +38%. Average percent change from baseline is represented in FIGS. 6A and 6B where % change=100×[(Treatment Mean−Baseline)/Baseline].

Example 11: L-Ampicillin Treats Solid Tumors in Combination with Anti-PD-1

Tumors persist in the body because the malignant cells are not detected or targeted by T cells for destruction. The ability of T cells to effectively target tumor cells is frequently compromised in the tumor environment due to the overexpression by tumor cells of molecules that serve to act as immune checkpoints which are pairs of receptors and ligands that moderate and inhibit T cell activity. For this reason, developing immune checkpoint inhibitors has recently become a critical goal in cancer therapeutics. For example, programmed cell death protein-1 (PD-1) is a receptor on T cells that binds to a ligand (PDL-1) that is overexpressed by tumor cells thereby inhibiting T cell function. Monoclonal antibodies that bind to PD-1 or PD-L1 have been shown to be remarkably effective immune checkpoint inhibitors that reduce tumor size and improve prognosis in multiple cancers including melanoma, renal cell carcinoma, non-small cell lung cancer, bladder cancer, cervical cancer, gastric cancer, liver cancer, pancreatic cancer, and brain cancer. The therapeutic use of immune checkpoint inhibitors and the resulting increase in T cell activity has shown substantial effectiveness to enhance T cell anti-tumor activity and to increase tumor-infiltrating $CD4^+$ helper T cells and improve prognosis.

Because L-ampicillin elevates levels of T cells, it was hypothesized that L-ampicillin will be effective in treating solid tumors. To test this hypothesis, BALB/c mice (6 mice/arm, 4 arms) were implanted orthotopically in the left kidney capsule with the syngeneic tumor cell line RENCA (ATCC CRL-2947). Following 1 week of tumor growth, mice were treated for 3 weeks with anti-PD1 or its isotype control (BioXCell, West Lebanon, N.H., BE0146 and BE0089, respectively) every 4 days IP at a suboptimal dose (7 mg/kg) and L-ampicillin at 5 mg/kg daily by oral gavage. Doses were determined from previously determined in vivo data (Levingston and Young, 2017). The study arms are set forth in Table 3 below.

TABLE 3

| Group # | n | Test Article | Dosing Route | Dose (mg/kg) | Dosing Volume (ml/kg) | Schedule |
|---|---|---|---|---|---|---|
| 1 | 6 | IgG isotype control + | I.P. | 7 | 5 ml/kg | Q4D |
|   |   | L-ampicillin Vehicle | P.O. | 5 | 10 ml/kg | QD |
| 2 | 6 | anti-mouse PD-1 + | I.P. | 7 | 5 ml/kg | Q4D |
|   |   | L-ampicillin Vehicle | P.O. | 5 | 10 ml/kg | QD |
| 3 | 6 | IgG isotype control + | I.P. | 7 | 5 ml/kg | Q4D |
|   |   | L-ampicillin | P.O. | 5 | 10 ml/kg | QD |
| 4 | 6 | anti-mouse PD-1 + | I.P. | 7 | 5 ml/kg | Q4D |
|   |   | L-ampicillin | P.O. | 5 | 10 ml/kg | QD |

Body weights were obtained 3 times per week to determine treatment dose. Blood was collected weekly for measurement of lymphocyte profile (CD3, CD4, CD8, and immature T cell (CD4+CD8+ double positives, DPs). On the day of study termination, mice were euthanized and samples were collected as follows:
 a) Lungs for formalin-fixed, paraffin-embedded (FFPE) histological staining to detect metastasis of tumor cells;
 b) Left and right kidney weight;
 c) Tumor physical appearance and size.

Figure 7A:
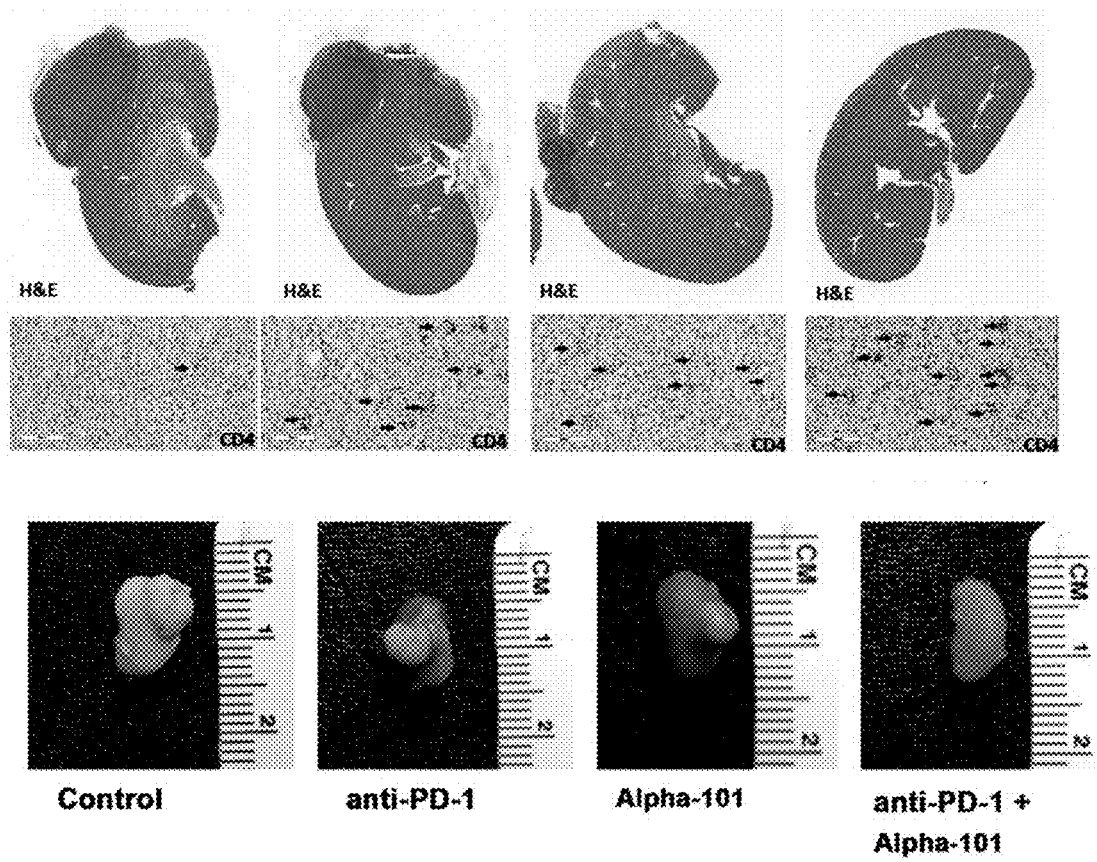
FIG. 7A are photographs of representative tumors treated with L-ampicillin or with anti-PD-1 or with L-ampicillin in combination with anti-PD-1.
Figure 7B:
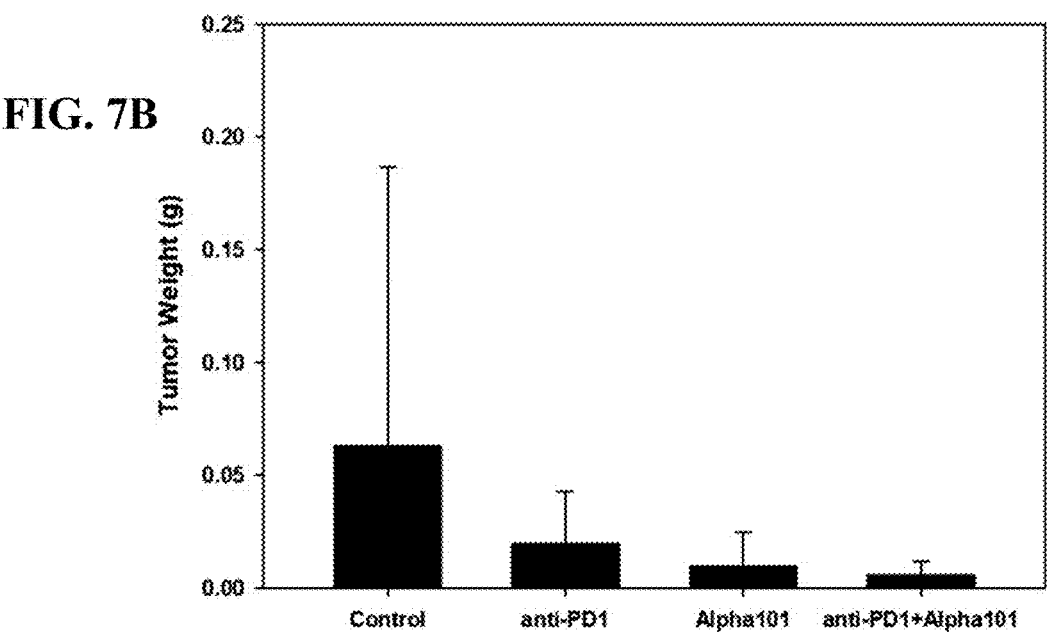
FIG. 7B are bar graphs showing the mean tumor weight within each group determined as the difference between the left kidney weight and the right kidney weight in each mouse

There were detectable tumors in untreated mice, mice treated with anti-PD-1, and mice treated with L-ampicillin (FIGS. 7A and 7B). In contrast, there were no detectable tumors in any of the 6 mice treated with the combination of anti-PD-1 and L-ampicillin. There were no adverse effects detected from treatment.

Excised kidneys were visually examined and photographed. Representative tumors are depicted in FIG. 7A. Mean tumor weight within each group was determined as the difference between the left kidney weight and the right kidney weight in each mouse (FIG. 7B).

Example 12: Physical Properties

D-ampicillin (CAS no. 69-53-4) and L-ampicillin (CAS no. 19379-33-0) are diastereomers. In biological systems, drugs that are diastereomers exhibit different chemical reactions, e.g., D-ampicillin is soluble in ethanol whereas L-ampicillin is not.

Figure 8A:
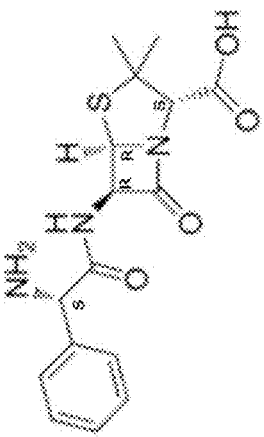
FIG. 8A and FIG. 8B are diagrams showing the absolute configuration of D-ampicillin (8A) and L-ampicillin (8B).
Figure 8B:
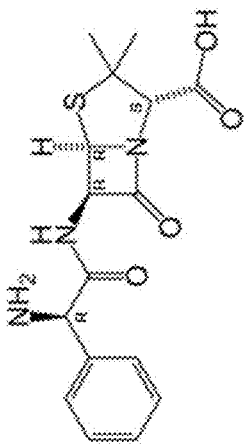

The absolute configuration of D-ampicillin and L-ampicillin are depicted in FIGS. 8A and 8B, respectively.

REFERENCE LIST

Ali, H., Tomhave, E. D., Richardson, R. M., Haribabu, B., and Snyderman, R. (1996). Thrombin primes responsiveness of selective chemoattractant receptors at a site distal to G protein activation. J. Biol. Chem. 271, 3200-3206.

Fagerberg, L., Hallström, B. M., Oksvold, P., Kampf, C., Djureinovic, D., Odeberg, J., Habuka, M., Tahmasebpoor, S., Danielsson, A., Edlund, K., Asplund, A., Sjöstedt, E., Lundberg, E., Szigyarto, C. A.-K., Skogs, M., Takanen, J. O., Berling, H., Tegel, H., Mulder, J., Nilsson, P., Schwenk, J. M., Lindskog, C., Danielsson, F., Mardinoglu, A., Sivertsson, von Feilitzen, K., Forsberg, M., Zwahlen, M., Olsson, I., Navani, S., Huss, M., Nielsen, J., Ponten, F., and Uhlén, M. (2014). Analysis of the Human Tissue-specific Expression by Genome-wide Integration of Transcriptomics and Antibody-based Proteomics. Mol. Cell. Proteomics 13, 397-406.

Bristow, C. L. (2001). Slow human immunodeficiency virus (HIV) infectivity correlated with low HIV coreceptor levels. Clin. Diagn. Lab. Immunol. 8, 932-936.

Bristow, C. L., Babayeva, M. A., LaBrunda, M., Mullen, M. P., and Winston, R. (2012). α1Proteinase Inhibitor regulates CD4+ lymphocyte levels and is rate limiting in HIV-1 disease. PLoS One 7, e31383.

Bristow, C. L., Cortes, J., Mukhtarzad, R., Trucy, M., Franklin, A., Romberg, V., and Winston, R. (2010). α1Antitrypsin therapy increases CD4+ lymphocytes to normal values in HIV-1 patients. In Soluble Factors Mediating Innate Immune Responses to HIV Infection, M. Alfano, ed. Bentham Science Publishers, Bristow, C. L., di Meo, F., and Arnold, R. R. (1998). Specific activity of α1proteinase inhibitor and α2 macroglobulin in human serum: Application to insulin-dependent diabetes mellitus. Clin. Immunol. Immunopathol. 89, 247-259.

Bristow, C. L. and Flood, P. M. (1993). T cell antigen receptor immune complexes demonstrating biologic and proteolytic activity. Int Immunol 5, 79-88.

Bristow, C. L., Mercatante, D. R., and Kole, R. (2003). HIV-1 preferentially binds receptors co-patched with cell surface elastase. Blood 102, 4479-4486.

Bristow, C. L., Modarresi, R., Babayeva, M. A., LaBrunda, M., Mukhtarzad, R., Trucy, M., Franklin, A., Reeves, R. E., Long, A., Mullen, M. P., Cortes, J., and Winston, R. (2013). A feedback regulatory pathway between LDL and alpha-1 proteinase inhibitor in chronic inflammation and infection. Discov. Med. 16, 201-218.

Bristow, C. L., Patel, H., and Arnold, R. R. (2001). Self-antigen prognostic for human immunodeficiency virus disease progression. Clin Diagn. Lab. Immunol. 8, 937-942.

Bristow, C. L., Wolkowicz, R., Trucy, M., Franklin, A., Di Meo, F., Kozlowski, M. T., Winston, R., and Arnold, R. R. (2008). NF-dB Signaling, Elastase Localization, and Phagocytosis Differ in HIV-1 Permissive and No permissive U937 Clones. J. Immunol. 180, 492-499.

Cao, C., Lawrence, D. A., Li, Y., Von Amin, C. A., Hers, J., Su, E. J., Makarova, A., Hyman, B. T., Strickland, D. K., and Zhang, L. (2006). Endocytic receptor LRP together with tPA and PAI-1 coordinates Mac-1-dependent macrophage migration. EMBO J. 25, 1860-1870.

CLSI. M100-S24: Performance Standards for Antimicrobial Susceptibility Testing; Twenty-Fourth Informational Supplement, 2014.

Dementiev, A., Dobo, J., and Gettins, P. G. W. (2006). Active Site Distortion Is Sufficient for Proteinase Inhibition by Serpins: Structure of the covalent complex of al-proteinase inhibitor with porcine pancreatic elastase. Journal of Biological Chemistry 281, 3452-3457.

Fagerberg, L., Hallström, B. M., Oksvold, P., Kampf, C., Djureinovic, D., Odeberg, J., Habuka, M., Tahmasebpoor, S., Danielsson, A., Edlund, K., Asplund, A., Sjöstedt, E., Lundberg, E., Szigyarto, C. A.-K., Skogs, M., Takanen, J. O., Berling, H., Tegel, H., Mulder, J., Nilsson, P., Schwenk, J. M., Lindskog, C., Danielsson, F., Mardinoglu, A., Sivertsson, +., von Feilitzen, K., Forsberg, M., Zwahlen, M., Olsson, I., Navani, S., Huss, M., Nielsen, J., Ponten, F., and Uhlén, M. (2014). Analysis of the Human Tissue-specific Expression by Genome-wide Integration of Transcriptomic and Antibody-based Proteomics. Mol. Cell. Proteomics 13, 397-406.

Garwicz, D., Lennartsson, A., Jacobsen, S. E. W., Gullberg, U., and Lindmark, A. (2005). Biosynthetic profiles of neutrophil serine proteases in a human bone marrow-derived cellular myeloid differentiation model. Haematologica 90, 38-44.

Gullberg, U., Lindmark, A., Lindgren, G., Persson, A. M., Nilsson, E., and Olsson, I. (1995). Carboxyl-terminal prodomain-deleted human leukocyte elastase and cathepsin G are efficiently targeted to granules and enzymatically activated in the rat basophilic/mast cell line RBL. J. Biol. Chem. 270, 12912-12918.

Holmes, M. V., Harrison, S., Talmud, P. J., Hingorani, A. D., and Humphries, S. E. (2011). Utility of genetic determinants of lipids and cardiovascular events in assessing risk. Nat Rev Cardiol 8, 207-221.

Janciauskiene, S., Moraga, F., and Lindgren, S. (2001). C-terminal fragment of [alpha] 1-antitrypsin activates human monocytes to a pro-inflammatory state through interactions with the CD36 scavenger receptor and LDL receptor. Atherosclerosis 158, 41-51.

Kindzelskii, A. L. and Petty, H. R. (2003). Intracellular Calcium Waves Accompany Neutrophil Polarization, Formylmethionylleucylphenylalanine Stimulation, and Phagocytosis: A High Speed Microscopy Study. J. Immunol. 170, 64-72.

Kounnas, M. Z., Church, F. C., Argraves, W. S., and Strickland, D. K. (1996). Cellular internalization and degradation of antithrombin III-thrombin, heparin cofactor II-thrombin, and alpha 1-antitrypsin-trypsin complexes is mediated by the low density lipoprotein receptor-related protein. J. Biol. Chem. 271, 6523-6529.

Lapidot, T. and Petit, I. (2002). Current understanding of stem cell mobilization: The roles of chemokines, proteolytic enzymes, adhesion molecules, cytokines, and stromal cells. Exp. Hematol. 30, 973-981.

Levingston, C. A. and Young, M. R. (2017). Transient immunological and clinical effectiveness of treating mice bearing premalignant oral lesions with PD-1 antibodies. Int. J. Cancer 140, 1609-1619.

Mashiba, S., Wada, Y., Takeya, M., Sugiyama, A., Hamakubo, T., Nakamura, A., Noguchi, N., Niki, E., Izumi, A., Kobayashi, M., Uchida, K., and Kodama, T. (2001). In Vivo complex formation of oxidized al-antitrypsin and LDL. Arterioscler. Thromb. Vasc. Biol. 21, 1801-1808.

Messmer, D., Jacque, J. M., Santisteban, C., Bristow, C. L., Han, S. Y., Villamide-Herrera, L., Mehlhop, E. R., Marx, P. A., Steinman, R. M., Gettie, A., and Pope, M. (2002). Endogenously expressed nef uncouples cytokine and chemokine production from membrane phenotypic maturation in dendritic cells. J. Immunol. 169, 4172-4182.

Modarresi, R., Xiang, Z., Yin, M., and Laurence, J. (2009). WNT/□-Catenin Signaling Is Involved in Regulation of Osteoclast Differentiation by Human Immunodeficiency Virus Protease Inhibitor Ritonavir: Relationship to Human Immunodeficiency Virus-Linked Bone Mineral Loss. Am. J. Pathol. 174, 123-135.

Navia, M. A., Springer, J. P., Lin, T. Y., Williams, H. R., Firestone, R. A., Pisano, J. M., Doherty, J. B., Finke, P. E., and Hoogsteen, K. (1987). Crystallographic study of a β-lactam inhibitor complex with elastase at 1.84 Å resolution. Nature 327, 79-82.

Stalenhoef, A. F., Malloy, M. J., Kane, J. P., and Havel, R. J. (1984). Metabolism of apolipoproteins B-48 and B-100 of triglyceride-rich lipoproteins in normal and lipoprotein lipase-deficient humans. PNAS 81, 1839-1843.

Tavor, S., Petit, I., Porozov, S., Goichberg, P., Avigdor, A., Sagiv, S., Nagler, A., Naparstek, E., and Lapidot, T. (2005). Motility, proliferation, and egress to the circulation of human AML cells are elastase dependent in NOD/SCID chimeric mice. Blood 106, 2120-2127.

Tyagi, S. C. (1991). Reversible inhibition of neutrophil elastase by thiol-modified α1-protease inhibitor. J. Biol. Chem. 266, 5279-5285.

Veniant, M., Zlot, C. H., Walzem, R. L., Pierotti, V., Driscoll, R., Dichek, D., Herz, J., and Young, S. G. (1998). Lipoprotein clearance mechanisms in LDL receptor-deficient "Apo-B48-only" and "Apo-B100-only" mice. J. Clin. Invest. 102, 1559-1568.

Wolf, K., Muller, R., Borgmann, S., Brocker, E. B., and Friedl, P. (2003). Amoeboid shape change and contact guidance: T-lymphocyte crawling through fibrilar collagen is independent of matrix remodeling by MMPs and other proteases. Blood 102, 3262-3269.

Wright, S. D. and Meyer, B. C. (1986). Phorbol esters cause sequential activation and deactivation of complement receptors on polymorphonuclear leukocytes. J. Immunol. 136, 1759-

Berge, S. M., Bighley, L. D., and Monkhouse, D. C. Pharmaceutical salts. J. Pharm. Sci. 66, 1-19. 1977.

Paulekuhn, G. S., Dressman, J. B., and Saal, C. (2007). Trends in Active Pharmaceutical Ingredient Salt Selection based on Analysis of the Orange Book Database. J. Med. Chem. 50, 6665-6672.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

What is claimed is:

1. A method of treating emphysema which comprises administering to a patient in need of such treatment a tromethamine salt of L-ampicillin that has substantially no bactericidal activity.

2. A method of treating COPD which comprises administering to a patient in need of such treatment a tromethamine salt of L-ampicillin that has substantially no bactericidal activity.

3. A method of treating emphysema which comprises administering to a patient in need of such treatment a pharmaceutical composition comprising a tromethamine salt of L-ampicillin that has substantially no bactericidal activity.

4. A method of treating COPD which comprises administering to a patient in need of such treatment a pharmaceutical composition comprising a tromethamine salt of L-ampicillin that has substantially no bactericidal activity.

* * * * *